United States Patent [19]

Sauers

[11] 4,454,334

[45] Jun. 12, 1984

[54] BENZYLSULFONYL ISOCYANATES

[75] Inventor: Richard F. Sauers, Hockessin, Del.

[73] Assignee: E. I. Du Pont de Nemours and Company, Wilmington, Del.

[21] Appl. No.: 534,155

[22] Filed: Sep. 21, 1983

Related U.S. Application Data

[60] Division of Ser. No. 370,138, Apr. 22, 1982, Pat. No. 4,420,325, which is a continuation-in-part of Ser. No. 306,212, Sep. 29, 1981, abandoned, which is a continuation-in-part of Ser. No. 203,638, Nov. 3, 1980, abandoned.

[51] Int. Cl.³ .......................................... C07C 143/828
[52] U.S. Cl. ................................................ 560/12
[58] Field of Search ........................................ 560/12

[56] References Cited

U.S. PATENT DOCUMENTS

| | | | |
|---|---|---|---|
| 4,238,621 | 12/1980 | Levitt | 560/12 |
| 4,371,391 | 2/1983 | Levitt | 71/93 |
| 4,394,153 | 7/1983 | Levitt | 71/92 |

Primary Examiner—Paul M. Coughlan, Jr.

[57] ABSTRACT

This invention relates to benzylsulfonylureas which are active pre- and post-emergence herbicides.

1 Claim, No Drawings

BENZYLSULFONYL ISOCYANATES

RELATED APPLICATIONS

This application is a divisional of copending application Ser. No. 370,138, filed Apr. 22, 1982, now U.S. Pat. No. 4,420,325, which is in turn a continuation-in-part of my copending application U.S. Ser. No. 306,212, filed Sept. 29, 1981, now abandoned, which is in turn a continuation-in-part of copending application U.S. Ser. No. 203,638, filed Nov. 3, 1980, now abandoned.

BACKGROUND OF THE INVENTION

This invention relates to novel benzylsulfonylureas. The compounds of this invention and their agriculturally suitable salts, are useful as agricultural chemicals, e.g., herbicides.

Netherlands Pat. No. 121,788, published Sept. 15, 1966, discloses the preparation of compounds of the following Formula and their use as general or selective herbicides:

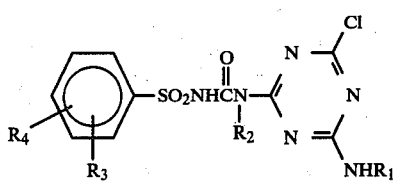

wherein
$R_1$ and $R_2$ may independently be alkyl of 1–4 carbon atoms; and
$R_3$ and $R_4$ may independently be hydrogen, chlorine or alkyl of 1–4 carbon atoms.

U.S. Pat. No. 3,637,366 discloses compounds having the formula:

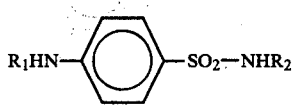

wherein
$R_1$ is hydrogen or lower saturated aliphatic acyl; and
$R_2$ is hydrogen, 2-pyrimidinyl, pyridyl, amidino, acetyl or carbamoyl.

The disclosed compounds are said to provide control of crabgrass, cress, endive, clover and *Poa annua*.

French Pat. No. 1,468,747 discloses the following para-substituted phenylsulfonamides as being useful as antidiabetic agents:

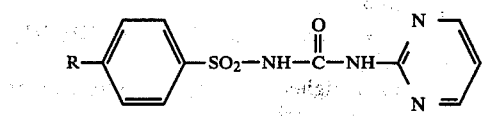

wherein R=H, halogen, $CF_3$ or alkyl.

Logemann et al., Chem. Ab., 53, 18052g (1959), disclose a number of sulfonamides, including uracil derivatives and those having the formula:

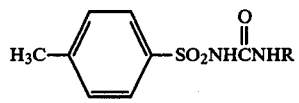

wherein
R is butyl, phenyl or

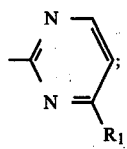

and
$R_1$ is hydrogen or methyl.
When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

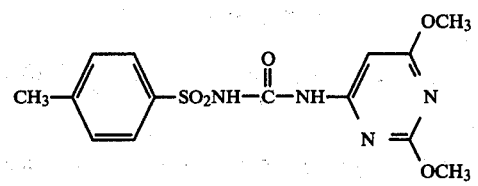

Based upon similarity to a known compound, the author speculated that the foregoing compound might have a hypoglycemic activity.

Substituted-pyrimidinyl sulfonylureas of the following formula, which are also para-substituted on the phenyl ring, are disclosed in Farmco Ed. Sco., 12, 586 (1957) [Chem. Ab., 53, 18052 g (1959)]:

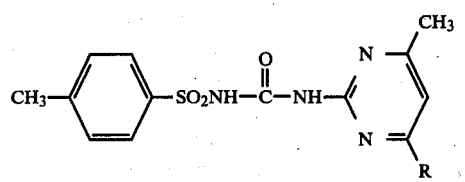

wherein R=H or $CH_3$.

U.S. Pat. No. 4,127,405 teaches compounds which are useful for controlling weeds in wheat having the formula:

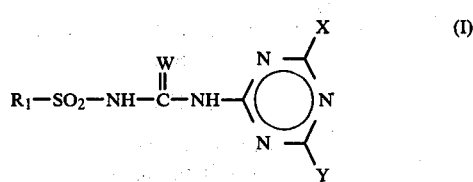

wherein
$R_1$ is

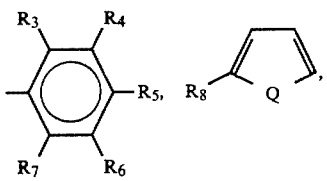

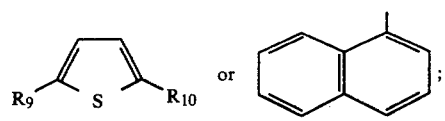

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S$— or $CH_3OCH_2$—; and Y is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Preventing or minimizing loss of a portion of such valuable crops by killing, or inhibiting the growth of undesired vegetation is one way of improving this efficiency. A wide variety of materials useful for killing or inhibiting (controlling) the growth of undesired vegetation is available; such materials are commonly referred to as herbicides. The need still exists however, for more effective herbicides.

SUMMARY OF THE INVENTION

This invention relates to compounds of Formula I and their agriculturally suitable salts, suitable agricultural compositions containing them, and their method-of-use as general and selective pre- and/or post-emergence herbicides and as plant growth regulants.

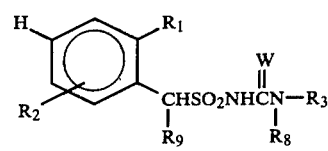

wherein $R_1$ is F, Cl, Br, $CF_3$, $C_1$-$C_3$ alkoxy, $C_1$-$C_3$ alkyl, $NO_2$, $CO_2R_4$, $SO_2R_5$, $SO_2NR_6R_7$, $SO_2N(OCH_3)CH_3$, $SO_2OCH_2CF_3$, $OSO_2R_5$ or $CH_2L$;

L is $SO_2NR_6R_7$, $OCH_3$, $OC_2H_5$, $CO_2CH_3$ or $CO_2C_2H_5$;

$R_2$ is H, Cl, Br, F, $CF_3$ or $OCH_3$;

$R_4$ is $C_1$-$C_3$ alkyl, $CH_2CH=CH_2$, $CH_2CH_2Cl$, or $CH_2CH_2OCH_3$;

$R_5$ is $C_1$-$C_3$ alkyl or $CF_3$;

$R_6$ and $R_7$ are independently $C_1$-$C_3$ alkyl;

$R_8$ is H or $CH_3$;

$R_9$ is H or $C_1$-$C_3$ alkyl;

$R_3$ is

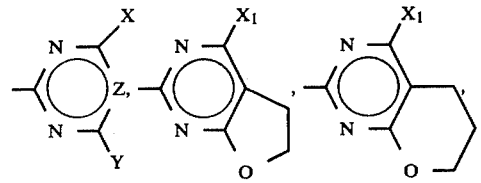

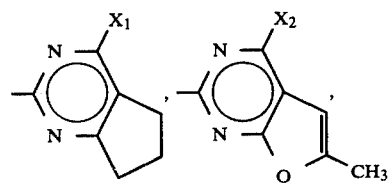

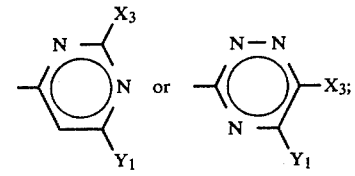

W is O or S;

X is $CH_3$, $OCH_3$ or Cl;

Y is $CH_3$, $C_2H_5$, $OCH_3$, $OC_2H_5$, $CH_2OCH_3$, $NH_2$, $NHCH_3$ or $N(CH_3)_2$;

Z is CH or N;

$X_1$ is H, Cl, $CH_3$, $OCH_3$ or $OC_2H_5$;

$X_2$ is $CH_3$, $C_2H_5$, $OCH_3$ or $OC_2H_5$;

$X_3$ is $CH_3$ or $OCH_3$; and $Y_1$ is $CH_3$ or $OCH_3$;

and their agriculturally suitable salts; provided that:

(1) when W is S, then $R_8$ is H;

(2) the total number of carbon atoms of $R_6$ and $R_7$ is less than or equal to 4; and (3) when X is Cl, then Z is CH and Y is $NH_2$, $NHCH_3$, $N(CH_3)_2$ or $OCH_3$.

Preferred for their higher herbicidal activity and/or more favorable ease of synthesis are:

(1) Compounds of Formula I wherein $R_2$ is H;

$R_8$ is H; and

W is O;

(2) Compounds of Preferred (1) wherein $R_1$ is $CF_3$, $NO_2$, $C_1$-$C_3$ alkoxy, $CO_2R_4$, $SO_2R_5$, $SO_2NR_6R_7$, $SO_2N(OCH_3)CH_3$ or $OSO_2R_5$;

$R_9$ is H;

$X_3$ is $OCH_3$; and $Y_1$ is $OCH_3$;

(3) Compounds of Preferred (2) wherein
$R_4$ is $CH_3$ or $C_2H_5$;
$R_5$ is $CH_3$ or $CF_3$; and
$R_6$ and $R_7$ are independently $CH_3$ or $C_2H_5$;

(4) Compounds of Preferred (3) wherein $R_3$ is

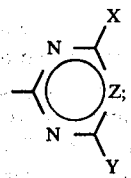

(5) Compounds of Preferred (4) wherein $R_1$ $CF_3$, $NO_2$, $CO_2CH_3$, $SO_2CH_3$, $SO_2N(CH_3)_2$, $SO_2N(OCH_3)CH_3$ or $OSO_2CH_3$; and (6) Compounds of Preferred (5) wherein X and Y are independently $CH_3$ or $OCH_3$.

Specifically preferred are:

N-[(4,6-dimethoxypyrimidin-2-yl)aminocarbonyl]-1-(2-nitrophenyl)methanesulfonamide, m.p. 207°-208°;

N-[(4,6-dimethoxy-1,3,5-triazin-2-yl)aminocarbonyl]-1-(2-nitrophenyl)methanesulfonamide, m.p. 185°-188°;

N-[(4-methoxy-6-methylpyrimidin-2-yl)aminocarbonyl]-1-(2-nitrophenyl)methanesulfonamide, m.p. 194°-195°;

N-[(4-methoxy-6-methyl-1,3,5-triazin-2-yl)aminocarbonyl]-1-(2-nitrophenyl)methanesulfonamide, m.p. 165°-168°;

N-[(4,6-dimethylpyrimidin-2-yl)aminocarbonyl]-1-(2-nitrophenyl)methanesulfonamide, m.p. 192°-194°;

2-[[(4,6-dimethoxypyrimidin-2-yl)aminocarbonyl]aminosulfonylmethyl]benzoic acid, methyl ester, m.p. 179°-183°;

2-[[(4,6-dimethoxy-1,3,5-triazin-2-yl)aminocarbonyl]aminosulfonylmethyl]benzoic acid, methyl ester, m.p. 154°-156°;

2-[[(4-methoxy-6-methylpyrimidin-2-yl)aminocarbonyl]aminosulfonylmethyl]benzoic acid, methyl ester, m.p. 162°-165°;

2-[[(4-methoxy-6-methyl-1,3,5-triazin-2-yl)aminocarbonyl]aminosulfonylmethyl]benzoic acid, methyl ester, m.p. 135°-140°;

2-[[(4,6-dimethylpyrimidin-2-yl)aminocarbonyl]aminosulfonylmethyl]benzoic acid, methyl ester, m.p. 165°-167°;

2-[[(4,6-dimethyl-1,3,5-triazin-2-yl)aminocarbonyl]aminosulfonylmethyl]benzoic acid, methyl ester, m.p. 125°-130°; and N-[(4,6-dimethoxypyrimidin-2-yl)aminocarbonyl]-1-(2-methylsulfonyloxyphenyl)methanesulfonamide, m.p. 202°-204°(d).

This invention also relates to compounds of Formula II which are useful intermediates for the preparation of the herbicidal compounds of Formula I:

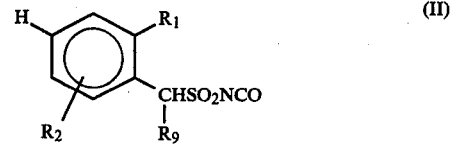

wherein
$R_1$ is F, Cl, Br, $CF_3$, $C_1$-$C_3$ alkoxy, $C_1$-$C_3$ alkyl, $NO_2$, $CO_2R_4$, $SO_2R_5$, $SO_2NR_6R_7$, $SO_2N(OCH_3)CH_3$, $SO_2OCH_2CF_3$, $OSO_2R_5$ or $CH_2L$;

L is $SO_2NR_6R_7$, $OCH_3$, $OC_2H_5$, $CO_2CH_3$ or $CO_2C_2H_5$;

$R_2$ is H, Cl, Br, F, $CF_3$ or $OCH_3$;

$R_4$ is $C_1$-$C_3$ alkyl, $CH_2CH=CH_2$, $CH_2CH_2Cl$, or $CH_2CH_2OCH_3$;

$R_5$ is $C_1$-$C_3$ alkyl or $CF_3$;

$R_6$ and $R_7$ are independently $C_1$-$C_3$ alkyl; and $R_9$ is H or $C_1$-$C_3$ alkyl;

provided that the total number of carbon atoms of $R_6$ and $R_7$ is less than or equal to 4.

Preferred intermediates for their more favorable ease of synthesis and/or the higher herbicidal activity of the derived products are:

(1) Compounds of Formula II wherein $R_2$ is H;

(2) Compounds of Preferred (1) wherein $R_1$ is $CF_3$, $NO_2$, $C_1$-$C_3$ alkoxy, $CO_2R_4$, $SO_2R_5$, $SO_2NR_6R_7$, $SO_2N(OCH_3)CH_3$ or $OSO_2R_5$; and (3) Compounds of Preferred (2) wherein
$R_4$ is $CH_3$ or $C_2H_5$;
$R_5$ is $CH_3$ or $CF_3$; and
$R_6$ and $R_7$ are independently $CH_3$ or $C_2H_5$.

Especially preferred as a selective herbicide for rice are compounds of the following formula:

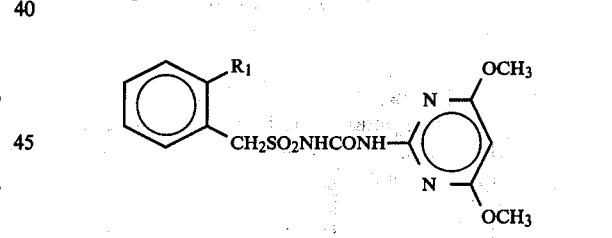

wherein $R_1$ is Cl, $NO_2$, $CO_2CH_3$, $SO_2CH_3$ $OSO_2CH_3$ or $SO_2N(CH_3)_2$

SYNTHESIS

The compounds of Formula I, where W=O, may be prepared as shown below in Equation 1 by the reaction of an appropriate benzenemethanesulfonyl isocyanate, II with an appropriate aminoheterocycle, III.

Equation 1

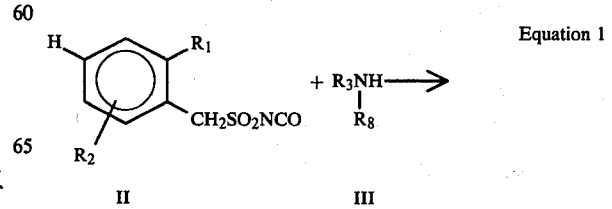

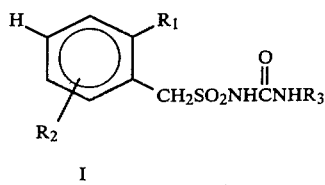

I wherein $R_1$, $R_2$, $R_3$, $R_8$ and $R_9$ are as previously defined.

The reaction of Equation 1 is best carried out in an inert aprotic solvent such as methylene chloride, tetrahydrofuran or acetonitrile at a temperature between 20° and 80°. A catalytic amount of 1,4-diazabicyclo[2,2,-2]octane (DABCO) may be used to accelerate the reaction. In cases in which the products are insoluble in the reaction solvent, they may be isolated by simple filtration. When the products are soluble, they may be isolated by evaporation of the solvent and trituration of the residue with solvents such as 1-chlorobutane, diethyl ether or methanol and filtration.

Compounds of Formula I in which W=S and $R_8$=H may be prepared by the reaction shown in Equation 2.

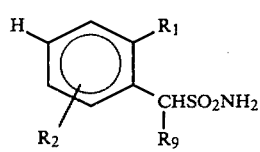 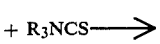

Equation 2

IV  V

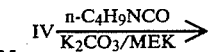

Ia wherein $R_1$, $R_2$, $R_3$, and $R_9$ are as previously defined.

The reaction of Equation 2 is best carried out by suspending the sulfonamide, the isothiocyanate and an equivalent of a base such as anhydrous potassium carbonate in a solvent such as acetone, methyl ethyl ketone, acetonitrile or ethyl acetate. The reaction is stirred at 25°–80° for 1 to 24 hours. In some cases, the product precipitates from the reaction mixture and can be filtered off, suspended in dilute mineral acid, filtered again and washed with cold water. If the product does not precipitate, it can be isolated by evaporation of the solvent, trituration of the residue with dilute mineral acid and filtration of the insoluble product.

The heterocyclic isothiocyanates, V, which are used in the procedure of Equation 2 are prepared according to the method of Japan Patent Application Pub. Kokai 51-143686, June 5, 1976; or that of W. Abraham and G. Barnikow, Tetrahedron 29, G91-7 (1973) both of which are herein incorporated by reference.

The benzenemethanesulfonyl isocyanates of Formula II may be prepared as shown in Equation 3, by phosgenation of the sulfonamides of Formula IV in the presence of butyl isocyanate. The sulfonyl isocyanates of Formula II may also be prepared, as shown in Equation 4, by phosgenation of the butyl ureas of Formula VI.

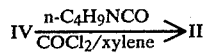

Equation 3 wherein $R_1$, $R_2$ and $R_9$ are as previously defined.

The above reaction is carried out by heating a mixture of the appropriate sulfonamide (IV), an alkyl isocyanate such as butyl isocyanate and a catalytic amount of a tertiary amine such as 1,4-diazabicyclo[2,2,2]octane (DABCO) in xylene, or other inert solvent of boiling point ≧135°, to approximately 135°. Phosgene is then added to the mixture over a 1–6 hour period at 125°–135° until an excess of phosgene is present as indicated by a permanent drop in the boiling point to less than 130°. The mixture is cooled and filtered to remove a small amount of insoluble by-products. The solvent and the alkyl isocyanate are distilled off in vacuo leaving a residue of the crude, sulfonyl isocyanate, II, which can be used without further purification.

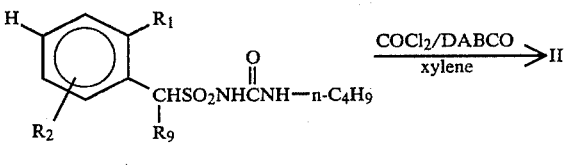

Equation 4

VI wherein $R_1$, $R_2$ and $R_9$ are as previously defined.

The compounds of Formula VI are conveniently prepared by stirring a mixture of the sulfonamides, IV, anhydrous potassium carbonate, and n-butyl isocyanate in acetone or methyl ethyl ketone at 25°–80° until all of the isocyanate has reacted. The products are isolated by quenching in dilute mineral acid and recrystallizing the solid product. The compounds VI are treated with phosgene and a catalytic amount of DABCO in refluxing xylene or chlorobenzene in a manner analogous to that described in Equation 3. The sulfonamides of Formula IV can be prepared from the appropriately substituted benzyl chlorides or benzyl bromides VII by the sequence of reactions described in Equation 5 below.

Equation 5

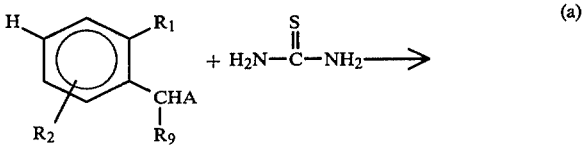

VII

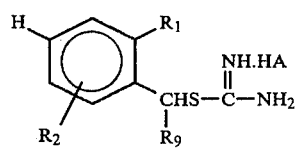

VIII

Equation 5
-continued

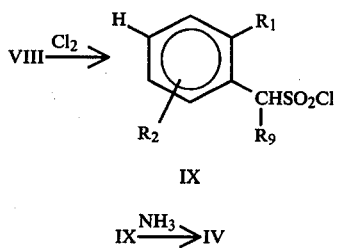

IX $$IX \xrightarrow{NH_3} IV \qquad (c)$$

wherein:
A is chlorine or bromine; and
$R_1$, $R_2$ and $R_9$ are as previously defined.

Equation (5a)

In Equation (5a) a benzyl halide of Formula VII is reacted with thiourea in protic solvents such as methanol or ethanol, or aprotic solvents such as methylene chloride or benzene. Temperatures of 40°–80° over one-half to 4 hours are typically required to complete the reaction. The product salts, VIII, are isolated by cooling and filtration or by concentration to remove the solvent. The salts, VIII, are generally sufficiently pure to be carried on directly to step (5b) without further purification.

Equation (5b)

In Equation (5b), the hydrochloride salts VIII (A=chlorine) are suspended in water and contacted with at least three equivalents of chlorine at between 5° and 20°. When the corresponding hydrobromide salts VIII (A=bromine) are used, it is generally advantageous to exchange the bromide ion for the nitrate ion before chlorination by treatment with an aqueous solution of one equivalent of silver nitrate; the precipitated silver bromide is removed by filtration and the filtrate treated as described above. The product sulfonyl chlorides of Formula IX are isolated by filtration and washing with water. No further purification of the sulfonyl chlorides IX is necessary.

Equation (5c)

In Equation (5c), the sulfonyl chlorides of Formula IX are suspended in an aprotic solvent such as diethyl ether, 1-chlorobutane, methylene chloride, or tetrahydrofuran and contacted with an excess of anhydrous ammonia at a temperature of 0° to 25°. The product sulfonamides of Formula IV are isolated by filtration and washing with water to remove the by-product ammonium chloride and concentrating the organic solution. Frequently, the crude sulfonamides may be used directly to prepare the sulfonyl isocyanates of Formula II. However, they may also be purified first by recrystallization from a suitable organic solvent such as ethanol, acetonitrile or chloroform.

The synthesis of heterocyclic amine derivatives such as those depicted by Formula III has been reviewed in "The Chemistry of Heterocyclic Compounds", a series published by Interscience Publ., New York and London. Aminopyrimidines are described by D. J. Brown in "The Pyrimidines", Vol. XVI of the above series.

The synthesis of the bicyclic pyrimidines of Formula III is described in the following references:
Braker, Sheehan, Spitzmiller and Lott, *J. Am. Chem. Soc.*, 69, 3072 (1947);
Mitter and Bhattacharya, *Quart. J. Indian. Chem. Soc.*, 4, 152 (1927);
Shrage and Hitchings, *J. Org. Chem.*, 16, 1153 (1951);
E. Bisayni et al., *Bull. Soc. Chem. Fr.*, 803 (1969);
Caldwell, Kornfeld and Donnell, *J. Am. Chem. Soc.*, 63, 2188 (1941); and
Fissekis, Myles and Brown, *J. Org. Chem.*, 29, 2670 (1964).

All of the above are herein incorporated by reference.

Agriculturally suitable salts of compounds of Formula I are also useful herbicides and can be prepared in a number of ways known to the art. For example, metal salts can be made by treating compounds of Formula I with a solution of an alkali or alkaline earth metal salts having a sufficiently basic anion (e.g. hydroxide, alkoxide, carbonate or hydride) quaternary amine salts can be made by similar techniques. Detailed examples of such techniques are given in U.S. Pat. No. 4,127,405, the disclosure of which is herein incorporated by reference.

The compounds of this invention and their preparation are further illustrated by the following examples wherein temperatures are given in degrees centigrade and all parts are by weight unless otherwise indicated.

EXAMPLE 1

2-Nitrophenylmethyl carbamidothioate hydrochloride

A solution of 153.9 g of o-nitrobenzylchloride and 68.5 g of thiourea in 900 ml of #2B ethanol was stirred at reflux temperature (80°) for 1¼ hours. The solution was cooled to 60° and 1.1 liters of 1-chlorobutane was added. Further cooling to 15° produced a heavy precipitate. The precipitate was filtered, washed with 1-chlorobutane and dried to yield 185.9 g of 2-nitrophenylmethyl carbamimidothioate hydrochloride, m.p. 190°–192°.

NMR (DMSO-$d_6$)$\delta$: 4.85 (s, 1.84, —$CH_2$—); 7.4–8.4 (m, 4.2H, 4 aromatics); 9.7 (broad singlet, 4.0H, 4 NH's).

EXAMPLE 2

2-Nitrophenylmethanesulfonyl chloride

To a suspension of 34.7 g of the product of Example 1 in 300 ml of water was added 24.0 ml of liquid chlorine at 10°–15° over a 45 minute period. After stirring an additional 30 minutes at 10°–12° the product was filtered off, washed with water and air dried in a fume hood overnight to give 31.6 g of 2-nitrophenylmethanesulfonyl chloride, m.p. 62.5°–64.0°.

EXAMPLE 3

2-Nitrophenylmethanesulfonamide

To a suspension of 29.4 g of the product of Example 2 in 250 ml of diethyl ether was added 6.5 ml of anhydrous ammonia at 5°–15°. After stirring at 15°–25° for 1 hour, the product was filtered off, washed with ether, and water and oven dried at 60° to give 20.5 g of 2-nitrophenylmethanesulfonamide, m.p.=134°–136°.

NMR (DMSO-$d_6$)$\delta$: 4.7 (s, 1.8H, —$CH_2$—); 6.8–7.3 (broad singlet, 1.8H, —$SO_2NH_2$); 7.5–8.3 (m, 4.4H, 4 aromatics).

EXAMPLE 4

2-Nitrophenylmethanesulfonyl isocyanate

A solution of 9.0 g of the product of Example 3, 4.2 g of butyl isocyanate and 0.1 g of DABCO in 80 ml of dry xylenes was heated to 136°. To this solution was added 3.0 ml of liquid phosgene at such a rate as to maintain the temperature between 125° and 136°. This addition required about 2½ hours. The solution was cooled to 25°, filtered under nitrogen and stripped in vacuo to give crude 2-nitrophenylmethanesulfonyl isocyanate as a viscous, moisture-sensitive oil showing a sulfonyl isocyanate peak in the infrared at 2230 cm$^{-1}$.

EXAMPLE 5

N-[(4,6-dimethoxypyrimidin-2-yl)aminocarbonyl]-1-(2-nitrophenyl)methanesulfonamide Under a nitrogen atmosphere, a mixture of 2.2 g of the product of Example 4, 0.9 g of 4,6-dimethoxy-2-aminopyrimidine and a few crystals of DABCO in 15 ml of dry acetonitrile was heated at 50°–55° for 1 hour, followed by stirring at room temperature overnight. The product was filtered, washed first with acetonitrile then 1-chlorobutane and oven dried in vacuo at 60° to give 1.8 g of N-[(4,6-dimethoxypyrimidin-2-yl)aminocarbonyl]-1-(2-nitrophenyl)methanesulfonamide, m.p.=207°–208°(d).

NMR (DMSO-d$_6$)δ: 3.8 (s, 6.1H, Het-OCH$_3$'s); 5.3 (s, 1.8H, —CH$_2$—); 6.0 (s, 1.0H, Het-H); 7.7–8.3 (m, 4.1H, 4 aromatics); 10.9 (s, 1.0 H, NH); ~12.5 (broad singlet, 0.9H, NH).

Anal. Calcd. for C$_{14}$H$_{15}$N$_5$O$_7$S: C, 42.31; H, 3.80; N, 17.63. Found: C, 42.6, 42.6; H, 3.9, 3.9; and N, 17.7, 17.8.

EXAMPLE 6

2-(Methylsulfonyl)phenylmethyl carbamimidothioate hydrobromide

A solution of 36.5 g of 2-(methylsulfonyl)benzyl bromide and 11.4 g of thiourea in 500 ml absolute ethanol was stirred at reflux temperature for 1½ hours and then allowed to cool to room temperature. Upon standing, the solution yielded white feather-like crystals which were collected by filtration, washed with cold 1-chlorobutane, and dried in vacuo. The yield of 2-(methylsulfonyl)phenylmethyl carbamimidothioate hydrobromide, m.p. 203°–206° C., was 36.3 g.

NMR (DMSO-d$_6$)δ: 3.3 (s, 3H, —CH$_3$); 4.9 (s, 2H, —CH$_2$—); 7.6–8.1 (m, 4H, aromatics); 9.4 (broad singlet, 4H, NH's).

EXAMPLE 7

2-(Methylsulfonyl)phenylmethanesulfonyl chloride

A solution of 29.5 g of the product from Example 6 in 450 ml water was reacted with 15.5 g of silver nitrate in 45 ml water. The resulting precipitate of silver bromide was removed by filtration and washed with 50 ml water. The aqueous filtrate was then diluted with 180 ml of glacial acetic acid and reacted with 15 ml of liquid chlorine at 0°–5° C., added over a period of 30 minutes. The reaction mixture was stirred for an additional 1¾ hours while the temperature was allowed to rise to 25° C. The light yellow solid was collected by filtration, washed with water and air-dried in a fume hood overnight to yield 22 g of 2-(methylsulfonyl)phenylmethanesulfonyl chloride which was used without further purification.

NMR (DMSO-d$_6$)δ: 3.4 (s, 3H, —CH$_3$); 4.4 (s, 2H, —CH$_2$—); 7.5–7.9 (m, 4H, aromatics).

EXAMPLE 8

2-(Methylsulfonyl)phenylmethanesulfonamide

To a suspension of 22 g of the product from Example 7 in 500 ml dry diethyl ether was added 25 ml anhydrous ammonia at 0°–5° C. The reaction mixture was stirred at 5°–15° C. for 45 minutes and then allowed to warm to room temperature over a one hour period. The solvent was removed in vacuo and the resulting solids were washed with water and ether. Further evaporation of the solvent in vacuo afforded 4.6 g of (2-methylsulfonyl)phenylmethanesulfonamide, m.p. 124°–127° C., as a tan solid.

NMR (DMSO-d$_6$)δ: 3.3 (s, 3H, —CH$_3$); 5.0 (s, 2H, —CH$_2$—); 7.6–7.8 (m, 3H, aromatics); 8.0 (m, 1H, aromatic).

IR(KBr): 3320, 3260, 1340, 1300, 1150 cm$^{-1}$.

EXAMPLE 9

N-[(n-butyl)aminocarbonyl]-2-(methylsulfonyl)phenylmethanesulfonamide

A mixture of 5.0 g of the product from Example 8, 4.2 g of anhydrous potassium carbonate, and 3.4 ml of n-butyl isocyanate in 60 ml methyl ethyl ketone was heated to reflux tiemperature for 5 hours. After cooling to room temperature, the solution was poured into 200 ml ice-water. This aqueous solution was acidified to ca. pH 1 by the slow addition of concentrated hydrochloric acid resulting in a white precipitate. The solids were filtered, washed with water, 1-chlorobutane, and then dried in a vacuum desiccator to give 6.2 g of N-[(n-butyl)aminocarbonyl]-2-(methylsulfonyl)phenylmethanesulfonamide as a tan solid, m.p. 149°–151° C. (dec.).

NMR (DMSO-d$_6$)δ: 0.9–1.6 (m, 7H, —CH$_2$CH$_2$CH$_3$); 3.0–3.2 (m, 2H, —CH$_2$—); 3.4 (s, 3H, —CH$_3$); 5.4 (s, 2H, —CH$_2$—); 6.6 (br s, 1H, N-H); 7.6–7.9 (m, 3H, aromatics); 8.0–8.2 (m, 1H, aromatic).

IR(KBr): 3350, 3250, 1700, 1320, 1150 cm$^{-1}$.

EXAMPLE 10

2-(Methylsulfonyl)phenylmethanesulfonyl isocyanate

A suspension of 5.5 g of the product from Example 9 and 0.1 g of 1,4-diazabicyclo[2.2.2]octane (DABCO) in 100 ml dry xylenes was heated to 125°–130° C. under an atmosphere of nitrogen. At this temperature, 2.5 ml of phosgene was added dropwise at a rate that maintained the temperature above 120° C. After completion of the addition (ca. one hour), the solution was heated at 125° C. for another two hours. After cooling to room temperature, the mixture was filtered under nitrogen and concentrated in vacuo to afford crude 2-(methylsulfonyl)phenylmethanesulfonyl isocyanate as a yellow semisolid which was carried on to the next step without purification. The IR spectrum of this intermediate displayed a characteristic isocyanate absorption at 2240 cm$^{-1}$.

EXAMPLE 11

N-[(4,6-Dimethoxypyrimidin-2-yl)aminocarbonyl]-2-(methylsulfonyl)phenylmethanesulfonamide To a solution of 3.0 g of the product from Example 10 in 30 ml dry dichloromethane was added 1.2 g of 4,6-dimethoxy-2-aminopyrimidine and the yellow homogeneous solution was stirred at room temperature overnight. The desired product, which had precipitated, was collected by filtration, washed with 1-chlorobutane, and dried in vacuo. The yield of N-[(4,6-dimethoxypyrimidin-2-yl)aminocarbonyl]-2-(methylsulfonyl)phenylmethanesulfonamide, m.p. 180°–182° C., was 2.4 g of white solid.

NMR (DMSO-d$_6$)δ: 3.8 (s, 6H, heterocyclic OCH$_3$'s); 5.4 (s, 2H, —CH$_2$—); 6.0 (s, 1H, heterocyclic H); 7.6–8.0 (m, 4H, aromatics); 10.6 (br s, 1H, N-H).

IR(KBr): 1730, 1610, 1580, 1370, 1350, 1150 cm$^{-1}$.

EXAMPLE 12

1-(2-Nitrophenyl)ethyl carbamimidothioate hydrobromide

A solution of 33.5 g of 1-(2-nitrophenyl)ethyl bromide and 11.4 g of thiourea in 375 ml absolute ethanol was stirred at reflux temperature for 3½ hours. The reaction mixture was allowed to cool to room temperature and was concentrated to one-half volume in vacuo. The solution was then cooled to ca. −60° C. and 1-chlorobutane was added until a gummy solid formed. The supernatant was decanted and the residue dried in vacuo to give 38 g of 1-(2-nitrophenyl)ethyl carbamimidothioate hydrobromide as a light orange solid which was not further purified.

NMR (DMSO-d$_6$)δ: 3.7 (br d, J=7 Hz, 3H, —CH$_3$); 5.5

(br q, J = 7Hz, 1H, —CH );

7.5–8.0 (m, 4H, aromatics); 9.4 (br s, 4H, N-H's).

EXAMPLE 13

1-(2-Nitrophenyl)ethanesulfonyl chloride

A solution of 37.6 g of the product from Example 12 in 700 ml water was reacted with 21.9 g of silver nitrate in 60 ml water. The resulting precipitate of silver bromide was removed by filtration and washed with water. Glacial acetic acid (250 ml) was added to the aqueous filtrate and this solution was cooled to 0° C. and treated with 23 ml of liquid chlorine, added over a period of about 45 minutes. After being stirred for one hour at 0°–5° C., the reaction mixture was allowed to warm to room temperature over an additional one hour period. The solids which had formed were filtered and washed with water. Air-drying overnight in a fume hood gave 27.5 g of 1-(2-nitrophenyl)ethanesulfonyl chloride as a light yellow solid.

NMR (DMSO-d$_6$)δ: 2.1 (d, J=7 Hz, 3H, —CH$_3$); 6.2

(q, J = 7Hz, 1H, —CH);

7.6–8.1 (m, 4H, aromatics);
IR(KBr): 1530, 1350, 1160 cm$^{-1}$.

EXAMPLE 14

1-(2-Nitrophenyl)ethanesulfonamide

Liquid anhydrous ammonia (10 ml) was added to a stirred suspension of the product from Example 13 in 350 ml dry diethyl ether at 0°–5° C. over a period of 20 minutes. The reaction mixture was stirred at 0°–5° C. for 30 minutes and was allowed to warm to room temperature over a two hour period. The solids were filtered and washed with diethy ether. Concentration of the filtrate in vacuo gave a yellow solid which was washed with water, 1-chlorobutane, and then dried under vacuum to yield 17 g of 1-(2-nitrophenyl)ethanesulfonamide as a pale yellow solid, m.p. 107°–109° C.

NMR (DMSO-d$_6$)δ: 1.7 (d, J=7 Hz, 3H, —CH$_3$); 5.0

(q, J = 7Hz, 1H, —CH);

7.0 (br s, 2H, NH$_2$); 7.4–8.0 (m, 4H, aromatics).
IR(KBr): 3340, 3260, 1350, 1310, 1160 cm$^{-1}$.

EXAMPLE 15

1-(2-Nitrophenyl)ethanesulfonyl isocyanate

A mixture of 16 g of the product from Example 14, 8.0 ml of n-butyl isocyanate, and 0.2 g of 1,4-diazabicyclo[2.2.2]octane (DABCO) in 125 ml dry xylenes was heated to 130°–135° C. for 1¼ hours. To this solution was added 6 ml of phosgene at a rate which maintained the temperature above 130° C. After completion of the addition (ca. one hour), the solution was cooled and filtered under nitrogen. The filtrate was concentrated in vacuo to give the crude 1-(2-nitrophenyl)ethanesulfonyl isocyanate as a viscous orange oil. The IR spectrum of this compound displayed a characteristic isocyanate absorption at 2240 cm$^{-1}$.

EXAMPLE 16

N-[(4,6-Dimethoxypyrimidin-2-yl)aminocarbonyl]-1-(2-nitrophenyl)ethanesulfonamide A solution of 4.0 g of the product from Example 15 and 2.2 g of 4,6-dimethoxy-2-aminopyrimidine in 29 ml dry acetonitrile was heated to ca. 60° C. for 1½ hours and then stirred at room temperature overnight. The product, which had precipitated, was collected and washed with 1-chlorobutane and then dried in vacuo. The yield of N-[(4,6-dimethoxypyrimidin-2-yl)aminocarbonyl]-1-(2-nitrophenyl)ethanesulfonamide was 3.1 g white solid, m.p. 168°–170° C.

NMR (DMSO-d$_6$)δ: 1.8 (d, J=7 Hz, 3H, —CH$_3$); 3.8 (s, 6H, heterocyclic OCH$_3$'s); 5.6 (q, J=7 Hz, 1H, (q, J = 7Hz, 1H, —CH);

5.8 (s, 1H, heterocyclic H); 7.6–8.0 (m, 4H, aromatics); 10.6 (br s, 1H, N-H).
IR(KBr): 1720, 1610, 1580, 1360, 1200, 1150 cm$^{-1}$.

Using the procedures and examples described above and choosing the appropriate aminoheterocyclic and sulfonyl isocyanate, the compounds described in Tables 1–8 may be prepared.

The sulfonylisocyanate intermediates described in Table 9 may also be prepared using the procedures and examples described above.

TABLE 1

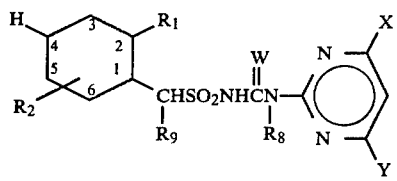

| R₁ | R₂ | W | R₈ | R₉ | X | Y | m.p. (°C.) |
|---|---|---|---|---|---|---|---|
| NO₂ | H | O | H | H | CH₃O | CH₃O | 207–208° (d) |
| NO₂ | H | O | H | H | CH₃O | CH₃ | 194–195° (d) |
| NO₂ | H | O | H | H | CH₃ | CH₃ | 192–194° (d) |
| Cl | H | O | H | H | CH₃O | CH₃O | 209–211° (d) |
| Cl | H | O | H | H | CH₃O | CH₃ | 184–185° (d) |
| Cl | H | O | H | H | CH₃ | CH₃ | 202–204° (d) |
| CO₂CH₃ | H | O | H | H | CH₃O | CH₃O | 179–183° |
| CO₂CH₃ | H | O | H | H | CH₃ | CH₃O | 162–165° |
| CO₂CH₃ | H | O | H | H | CH₃ | CH₃ | 165–167° |
| CH₃ | H | O | H | H | CH₃O | CH₃O | 214–216° (d) |
| CH₃ | H | O | H | H | CH₃ | CH₃O | 173–175° (d) |
| CH₃ | H | O | H | H | CH₃ | CH₃ | 192–193.5° (d) |
| F | H | O | H | H | CH₃O | CH₃ | |
| Br | H | O | H | H | CH₃O | CH₃ | |
| CH₃O | H | O | H | H | CH₃O | CH₃ | |
| CO₂—⟨ | H | O | H | H | CH₃O | CH₃ | |
| CO₂CH₂CH₂Cl | H | O | H | H | CH₃O | CH₃ | |
| CO₂CH₂CH=CH₂ | H | O | H | H | CH₃O | CH₃ | |
| CO₂CH₂CH₂OCH₃ | H | O | H | H | CH₃O | CH₃ | |
| CH₃SO₂— | H | O | H | H | CH₃O | CH₃ | |
| n-C₃H₇SO₂— | H | O | H | H | CH₃O | OCH₃ | 179–181° |
| CF₃SO₂ | H | O | H | H | CH₃O | CH₃ | |
| CF₃ | H | O | H | H | CH₃O | CH₃ | |
| SO₂N(OCH₃)(CH₃) | H | O | H | H | CH₃O | CH₃ | |
| CO₂C₂H₅ | H | O | H | H | CH₃ | CH₃ | |
| CO₂C₂H₅ | H | O | H | H | CH₃ | CH₃O | |
| CO₂C₂H₅ | H | O | H | H | CH₃O | CH₃O | |
| SO₂N(CH₃)₂ | H | O | H | H | CH₃O | CH₃ | 142–145° |
| SO₂N(CH₃)₂ | H | O | H | H | CH₃O | CH₃O | 167–170° |
| SO₂N(CH₂CH₃)(CH₃) | H | O | H | H | CH₃O | CH₃ | |
| SO₂N(⟨)(CH₃) | H | O | H | H | CH₃O | CH₃ | |
| CH₃SO₂O— | H | O | H | H | CH₃O | CH₃ | 169–171° (d) |
| n-C₃H₇SO₂O— | H | O | H | H | CH₃O | CH₃ | |
| CF₃SO₂O— | H | O | H | H | CH₃O | CH₃ | |
| NO₂ | 3-Cl | O | H | H | CH₃O | CH₃ | |
| NO₂ | 5-Cl | O | H | H | CH₃O | CH₃ | |
| NO₂ | 6-Cl | O | H | H | CH₃O | CH₃ | |
| NO₂ | 5-Br | O | H | H | CH₃O | CH₃ | |
| NO₂ | 5-F | O | H | H | CH₃O | CH₃ | |
| NO₂ | 5-CF₃ | O | H | H | CH₃O | CH₃ | |
| NO₂ | 5-OCH₃ | O | H | H | CH₃O | CH₃ | |
| CO₂CH₃ | 5-Cl | O | H | H | CH₃O | CH₃ | |
| CO₂CH₃ | 5-CF₃ | O | H | H | CH₃O | CH₃ | |
| CO₂CH₃ | 6-Cl | O | H | H | CH₃O | CH₃ | |
| CO₂CH₃ | 5-Br | O | H | H | CH₃O | CH₃ | |
| CO₂CH₃ | 5-F | O | H | H | CH₃O | CH₃ | |
| CO₂CH₃ | 5-OCH₃ | O | H | H | CH₃O | CH₃ | |
| CO₂CH₃ | H | O | H | H | CH₃ | CH₃CH₂O | |
| CO₂CH₃ | H | O | H | H | CH₃O | CH₃CH₂O | |
| CO₂CH₃ | H | O | H | H | CH₃ | CH₃OCH₂— | |
| CO₂CH₃ | H | O | H | H | CH₃O | CH₃OCH₂— | |
| CH₃SO₂O | H | O | H | H | CH₃O | CH₃O | 202–204° (d) |
| CH₃SO₂O | H | O | H | H | CH₃ | CH₃ | 172–178° (d) |
| CH₃SO₂ | H | O | H | H | CH₃O | CH₃O | 180–182° |
| NO₂ | H | O | H | CH₃ | CH₃O | CH₃O | 168–170° |

TABLE 1-continued

Structure: cyclohexane with H at position 4 (via C3, C4, C5), R1 at position 2, R2 at position 5 (via C6), and at C1: CHSO₂NHC(=W)N(R8)-pyrimidine ring with X and Y substituents; R9 on the CH.

| R₁ | R₂ | W | R₈ | R₉ | X | Y | m.p. (°C.) |
|---|---|---|---|---|---|---|---|
| NO₂ | H | O | H | CH₃ | CH₃O | CH₃ | 119–121° |
| NO₂ | H | O | H | CH₃ | CH₃ | CH₃ | 140–144° |
| NO₂ | H | S | H | H | CH₃O | CH₃ | |
| CO₂CH₃ | H | O | H | CH₂CH₃ | CH₃O | CH₃ | |
| CO₂CH₃ | H | O | H | i-C₃H₇ | CH₃O | CH₃ | |
| CO₂CH₃ | H | O | CH₃ | H | CH₃O | CH₃ | |
| CO₂CH₃ | H | O | H | H | Cl | CH₃O | |
| Cl | H | O | CH₃ | H | CH₃O | CH₃O | |
| Cl | H | S | H | H | CH₃O | CH₃ | |
| Cl | H | O | H | H | Cl | NH₂ | |
| Cl | H | O | H | H | Cl | NHCH₃ | |
| CH₃ | H | O | H | H | Cl | N(CH₃)₂ | |
| CH₃ | H | S | H | H | CH₃O | CH₃ | |
| CH₂CH₃ | H | O | CH₃ | H | CH₃O | CH₃O | |
| i-C₃H₇ | H | O | H | H | CH₃O | CH₃ | |
| SO₂OCH₂CF₃ | H | O | H | H | CH₃O | CH₃ | |
| CO₂CH₃ | H | O | H | H | CH₃O | CH₂CH₃ | |
| OCH₂CH₃ | H | O | H | H | CH₃O | CH₃ | |
| O—CH(CH₃)₂ (isopropoxy) | H | O | H | H | CH₃O | CH₃ | |
| CH₂SO₂N(CH₃)₂ | H | O | H | H | CH₃O | CH₃ | |
| CH₂SO₂N(CH₃)—CH(CH₃)₂ | H | O | H | H | CH₃O | CH₃ | |
| CH₂SO₂N(CH₃)Et | H | O | H | H | CH₃O | CH₃ | |
| CH₂OCH₃ | H | O | H | H | CH₃O | CH₃ | |
| CH₂OEt | H | O | H | H | CH₃O | CH₃ | |
| CH₂CO₂CH₃ | H | O | H | H | CH₃O | CH₃ | |
| CH₂CO₂Et | H | O | H | H | CH₃O | CH₃ | |
| OCH₃ | H | O | H | H | CH₃O | CH₃ | |
| CO₂CH₃ | H | O | H | H | CH₃O | NH₂ | |
| CO₂CH₃ | H | O | H | H | CH₃O | NHCH₃ | |
| CO₂CH₃ | H | O | H | H | CH₃O | N(CH₃)₂ | |
| CO₂CH₃ | H | O | H | H | CH₃ | NH₂ | |
| CO₂CH₃ | H | O | H | H | CH₃ | NHCH₃ | |
| CO₂CH₃ | H | O | H | H | CH₃ | N(CH₃)₂ | |
| CO₂CH₃ | H | O | H | H | CH₃ | CH₂CH₃ | |

TABLE 2

Structure: cyclohexane with H at position 4, R1 at position 2, R2 at position 5, and at C1: CHSO₂NHC(=W)N(R8)-triazine ring (N at positions 1,3,5) with X and Y substituents; R9 on the CH.

| R₁ | R₂ | W | R₈ | R₉ | X | Y | m.p. (°C.) |
|---|---|---|---|---|---|---|---|
| NO₂ | H | O | H | H | CH₃O | CH₃O | 185–188° (d) |
| NO₂ | H | O | H | H | CH₃O | CH₃ | 165–168° (d) |
| NO₂ | H | O | H | H | CH₃ | CH₃ | |
| Cl | H | O | H | H | CH₃O | CH₃O | 198–199° (d) |
| Cl | H | O | H | H | CH₃O | CH₃ | 193–195° (d) |
| Cl | H | O | H | H | CH₃ | CH₃ | 212–214° (d) |
| CO₂CH₃ | H | O | H | H | CH₃O | CH₃O | 154–156° |
| CO₂CH₃ | H | O | H | H | CH₃ | CH₃O | 135–140° |
| CO₂CH₃ | H | O | H | H | CH₃ | CH₃ | 125–130° |
| CH₃ | H | O | H | H | CH₃O | CH₃O | 185–189° (d) |
| CH₃ | H | O | H | H | CH₃ | CH₃O | 177–179° (d) |
| CH₃ | H | O | H | H | CH₃ | CH₃ | 197.5–199° (d) |
| F | H | O | H | H | CH₃O | CH₃ | |
| Br | H | O | H | H | CH₃O | CH₃ | |

TABLE 2-continued

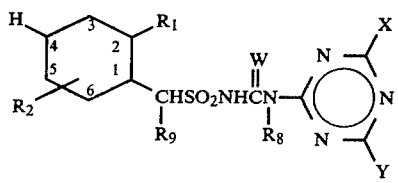

| R₁ | R₂ | W | R₈ | R₉ | X | Y | m.p. (°C.) |
|---|---|---|---|---|---|---|---|
| CH₃O | H | O | H | H | CH₃O | CH₃ | |
| CO₂—⟨ | H | O | H | H | CH₃O | CH₃ | |
| CO₂CH₂CH₂Cl | H | O | H | H | CH₃O | CH₃ | |
| CO₂CH₂CH=CH₂ | H | O | H | H | CH₃O | CH₃ | |
| CO₂CH₂CH₂OCH₃ | H | O | H | H | CH₃O | CH₃ | |
| CH₃SO₂— | H | O | H | H | CH₃O | CH₃ | 181–184° |
| n-C₃H₇SO₂— | H | O | H | H | CH₃O | CH₃ | 170–172° |
| CF₃SO₂ | H | O | H | H | CH₃O | CH₃ | |
| CF₃ | H | O | H | H | CH₃O | CH₃ | |
| SO₂N(OCH₃)CH₃ | H | O | H | H | CH₃O | CH₃ | |
| CO₂C₂H₅ | H | O | H | H | CH₃ | CH₃ | |
| CO₂C₂H₅ | H | O | H | H | CH₃ | CH₃O | |
| CO₂C₂H₅ | H | O | H | H | CH₃O | CH₃O | |
| SO₂N(CH₃)₂ | H | O | H | H | CH₃O | CH₃ | |
| SO₂N(CH₂CH₃)CH₃ | H | O | H | H | CH₃O | CH₃ | |
| SO₂N⟨CH₃ | H | O | H | H | CH₃O | CH₃ | |
| CH₃SO₂O— | H | O | H | H | CH₃O | CH₃ | 176–179° (d) |
| n-C₃H₇SO₂O— | H | O | H | H | CH₃O | CH₃ | |
| CF₃SO₂O— | H | O | H | H | CH₃O | CH₃ | |
| NO₂ | 3-Cl | O | H | H | CH₃O | CH₃ | |
| NO₂ | 5-Cl | O | H | H | CH₃O | CH₃ | |
| NO₂ | 6-Cl | O | H | H | CH₃O | CH₃ | |
| NO₂ | 5-Br | O | H | H | CH₃O | CH₃ | |
| NO₂ | 5-F | O | H | H | CH₃O | CH₃ | |
| NO₂ | 5-CF₃ | O | H | H | CH₃O | CH₃ | |
| NO₂ | 5-OCH₃ | O | H | H | CH₃O | CH₃ | |
| CO₂CH₃ | 5-Cl | O | H | H | CH₃O | CH₃ | |
| CO₂CH₃ | 5-CF₃ | O | H | H | CH₃O | CH₃ | |
| CO₂CH₃ | 6-Cl | O | H | H | CH₃O | CH₃ | |
| CO₂CH₃ | 5-Br | O | H | H | CH₃O | CH₃ | |
| CO₂CH₃ | 5-F | O | H | H | CH₃O | CH₃ | |
| CO₂CH₃ | 5-OCH₃ | O | H | H | CH₃O | CH₃ | |
| CO₂CH₃ | H | O | H | H | CH₃ | CH₃CH₂O | |
| CO₂CH₃ | H | O | H | H | CH₃O | CH₃CH₂O | |
| CO₂CH₃ | H | O | H | H | CH₃ | CH₃OCH₂— | |
| CO₂CH₃ | H | O | H | H | CH₃O | CH₃OCH₂— | |
| CH₃SO₂O | H | O | H | H | CH₃O | CH₃O | 187–192° (d) |
| CH₃SO₂O | H | O | H | H | CH₃ | CH₃ | 155–161° (d) |
| NO₂ | H | O | H | CH₃ | CH₃O | CH₃O | 166–169° |
| NO₂ | H | O | H | CH₃ | CH₃O | CH₃ | 147–149° |
| NO₂ | H | S | H | H | CH₃O | CH₃ | |
| NO₂ | H | O | CH₃ | H | CH₃O | CH₃ | |
| CO₂CH₃ | H | S | H | H | CH₃O | CH₃ | |
| CO₂CH₃ | H | O | H | CH₂CH₃ | CH₃O | CH₃ | |
| CO₂CH₃ | H | O | H | i-C₃H₇ | CH₃O | CH₃ | |
| CO₂CH₃ | H | O | CH₃ | H | CH₃O | CH₃ | |
| CO₂CH₃ | H | O | H | H | CH₃ | NH₂ | |
| CO₂CH₃ | H | O | H | H | CH₃O | NHCH₃ | |
| CO₂CH₃ | H | O | H | H | CH₃ | N(CH₃)₂ | |
| CO₂CH₃ | H | O | H | H | CH₃O | CH₂CH₃ | |
| CO₂CH₃ | H | O | H | H | CH₃ | CH₂CH₃ | |
| Cl | H | S | H | H | CH₃O | CH₃ | |
| Cl | H | O | H | H | CH₃O | NH₂ | |
| Cl | H | O | H | H | CH₃ | NHCH₃ | |
| Cl | H | O | H | H | CH₃O | N(CH₃)₂ | |

TABLE 2-continued

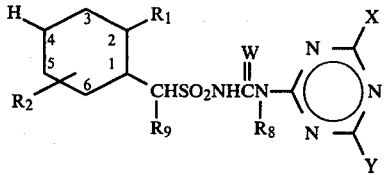

| R₁ | R₂ | W | R₈ | R₉ | X | Y | m.p. (°C.) |
|---|---|---|---|---|---|---|---|
| Cl | H | O | H | H | CH₃O | CH₂CH₃ | |
| CH₃ | H | S | H | H | CH₃O | CH₃ | |
| CH₃ | H | O | H | CH₃ | CH₃O | CH₃ | |
| CH₂CH₃ | H | O | H | H | CH₃O | CH₃ | |
| i-C₃H₇ | H | O | H | H | CH₃O | CH₃ | |
| SO₂OCH₂CF₃ | H | O | H | H | CH₃O | CH₃ | |
| OEt | H | O | H | H | CH₃O | CH₃ | |
| O—CH(CH₃)₂ | H | O | H | H | CH₃O | CH₃ | |
| CH₂SO₂N(CH₃)₂ | H | O | H | H | CH₃O | CH₃ | |
| CH₂SO₂N(CH₃)—CH(CH₃)₂ | H | O | H | H | CH₃O | CH₃ | |
| CH₂SO₂N(CH₃)Et | H | O | H | H | CH₃O | CH₃ | |
| CH₂OCH₃ | H | O | H | H | CH₃O | CH₃ | |
| CH₂OCH₂CH₃ | H | O | H | H | CH₃O | CH₃ | |
| CH₂CO₂CH₃ | H | O | H | H | CH₃O | CH₃ | |
| CH₂CO₂Et | H | O | H | H | CH₃O | CH₃ | |
| OCH₃ | H | O | H | H | CH₃O | CH₃ | |

TABLE 3

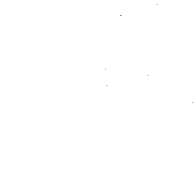

| R₁ | R₂ | W | R₈ | R₉ | X₁ | m.p. (°C.) |
|---|---|---|---|---|---|---|
| NO₂ | H | O | H | H | CH₃ | |
| NO₂ | H | O | H | H | CH₃O | |
| Cl | H | O | H | H | CH₃ | |
| Cl | H | O | H | H | CH₃O | |
| CO₂CH₃ | H | O | H | H | CH₃ | |
| CO₂CH₃ | H | O | H | H | CH₃O | |
| CH₃ | H | O | H | H | CH₃ | |
| F | H | O | H | H | CH₃ | |
| Br | H | O | H | H | CH₃ | |
| CO₂—CH(CH₃)₂ | H | O | H | H | CH₃ | |
| CH₃ | H | O | H | H | CH₃O | |
| CO₂CH₂CH₂Cl | H | O | H | H | CH₃ | |
| CO₂CH₂CH=CH₂ | H | O | H | H | CH₃ | |
| CO₂CH₂CH₂OCH₃ | H | O | H | H | CH₃ | |
| CH₃SO₂— | H | O | H | H | CH₃ | |
| n-C₃H₇SO₂— | H | O | H | H | CH₃ | |
| CF₃SO₂ | H | O | H | H | CH₃ | |
| CF₃ | H | O | H | H | CH₃ | |
| SO₂N(OCH₃)CH₃ | H | O | H | H | CH₃ | |
| SO₂N(CH₃)₂ | H | O | H | H | CH₃ | |

TABLE 3-continued

| R₁ | R₂ | W | R₈ | R₉ | X₁ | m.p. (°C.) |
|---|---|---|---|---|---|---|
| SO₂N(CH₃)—C₂H₅ | H | O | H | H | CH₃ | |
| SO₂N(CH₃)—CH(CH₃)₂ | H | O | H | H | CH₃— | |
| CH₃SO₂O— | H | O | H | H | CH₃— | |
| n-C₃H₇SO₂O— | H | O | H | H | CH₃— | |
| CF₃SO₂O— | H | O | H | H | CH₃— | |
| NO₂ | 3-Cl | O | H | H | CH₃— | |
| NO₂ | 5-Cl | O | H | H | CH₃— | |
| NO₂ | 6-Cl | O | H | H | CH₃— | |
| NO₂ | 5-Br | O | H | H | CH₃— | |
| NO₂ | 5-CF₃ | O | H | H | CH₃— | |
| NO₂ | 5-OCH₃ | O | H | H | CH₃— | |
| CO₂CH₃ | 5-Cl | O | H | H | CH₃— | |
| CO₂CH₃ | 5-CF₃ | O | H | H | CH₃— | |
| CO₂CH₃ | 6-Cl | O | H | H | CH₃— | |
| CO₂CH₃ | 5-Br | O | H | H | CH₃— | |
| CO₂CH₃ | 5-F | O | H | H | CH₃— | |
| CO₂CH₃ | 5-OCH₃ | O | H | H | CH₃— | |
| NO₂ | H | O | H | H | H | |
| CO₂CH₃ | H | O | H | H | H | |
| Cl | H | O | H | H | H | |
| SO₂N(CH₃)₂ | H | O | H | H | OCH₂CH₃ | |
| NO₂ | H | O | H | CH₃ | CH₃ | |
| NO₂ | H | S | H | H | H | |
| CO₂CH₃ | H | O | H | CH₃ | CH₃ | |
| CO₂CH₃ | H | O | H | CH₂CH₃ | CH₃O | |
| CO₂CH₃ | H | O | H | i-C₃H₇ | H | |
| CO₂CH₃ | H | O | CH₃ | H | CH₃ | |
| CO₂CH₃ | H | O | H | H | OCH₂CH₃ | |
| CO₂CH₃ | H | O | H | H | Cl | |
| Cl | H | S | H | H | H | |
| Cl | H | O | CH₃ | H | CH₃O | |
| Cl | H | O | H | H | Cl | |
| Cl | H | O | H | H | OCH₂CH₃ | |
| CH₃ | H | S | H | H | H | |
| CH₂CH₃ | H | O | H | H | CH₃ | |
| i-C₃H₇ | H | O | H | H | CH₃ | |
| SO₂OCH₂CF₃ | H | O | H | H | CH₃ | |
| OEt | H | O | H | H | CH₃ | |
| O—CH(CH₃)₂ | H | O | H | H | CH₃ | |
| CH₂SO₂N(CH₃)₂ | H | O | H | H | CH₃ | |
| CH₂SO₂N(CH₃)—CH(CH₃)₂ | H | O | H | H | CH₃ | |
| CH₂SO₂N(CH₃)Et | H | O | H | H | CH₃ | |
| CH₂OCH₃ | H | O | H | H | CH₃ | |
| CH₂OCH₂CH₃ | H | O | H | H | CH₃ | |
| CH₂CO₂CH₃ | H | O | H | H | CH₃ | |
| CH₂CO₂Et | H | O | H | H | CH₃ | |
| OCH₃ | H | O | H | H | CH₃ | |

TABLE 4

Structure: cyclohexane ring (positions 1-6) with H at position 4, R₁ at position 2, R₂ at position 5, and at position 1: -CHSO₂NHC(=W)N(R₈)-C(R₉)=N- fused to a benzofuran-like ring system with X₁ substituent.

| R₁ | R₂ | W | R₈ | R₉ | X₁ | m.p. (°C.) |
|---|---|---|---|---|---|---|
| NO₂ | H | O | H | H | CH₃ | |
| NO₂ | H | O | H | H | CH₃O | |
| Cl | H | O | H | H | CH₃ | |
| Cl | H | O | H | H | CH₃O | |
| CO₂CH₃ | H | O | H | H | CH₃ | |
| CO₂CH₃ | H | O | H | H | CH₃O | |
| CH₃ | H | O | H | H | CH₃ | |
| F | H | O | H | H | CH₃ | |
| Br | H | O | H | H | CH₃ | |
| CO₂-i-C₃H₇ | H | O | H | H | CH₃ | |
| CH₃ | H | O | H | H | CH₃O | |
| CO₂CH₂CH₂Cl | H | O | H | H | CH₃ | |
| CO₂CH₂CH=CH₂ | H | O | H | H | CH₃ | |
| CO₂CH₂CH₂OCH₃ | H | O | H | H | CH₃ | |
| CH₃SO₂— | H | O | H | H | CH₃ | |
| n-C₃H₇SO₂— | H | O | H | H | CH₃ | |
| CF₃SO₂ | H | O | H | H | CH₃ | |
| CF₃ | H | O | H | H | CH₃ | |
| SO₂N(CH₃)—OCH₃ | H | O | H | H | CH₃ | |
| SO₂N(CH₃)₂ | H | O | H | H | CH₃ | |
| SO₂N(CH₃)—C₂H₅ | H | O | H | H | CH₃ | |
| SO₂N(CH₃)—i-C₃H₇ | H | O | H | H | CH₃— | |
| CH₃SO₂O— | H | O | H | H | CH₃— | |
| n-C₃H₇SO₂O— | H | O | H | H | CH₃— | |
| CF₃SO₂O— | H | O | H | H | CH₃— | |
| NO₂ | 3-Cl | O | H | H | CH₃— | |
| NO₂ | 5-Cl | O | H | H | CH₃— | |
| NO₂ | 6-Cl | O | H | H | CH₃— | |
| NO₂ | 5-Br | O | H | H | CH₃— | |
| NO₂ | 5-CF₃ | O | H | H | CH₃— | |
| NO₂ | 5-OCH₃ | O | H | H | CH₃— | |
| CO₂CH₃ | 5-Cl | O | H | H | CH₃— | |
| CO₂CH₃ | 5-CF₃ | O | H | H | CH₃— | |
| CO₂CH₃ | 6-Cl | O | H | H | CH₃— | |
| CO₂CH₃ | 5-Br | O | H | H | CH₃— | |
| CO₂CH₃ | 5-F | O | H | H | CH₃— | |
| CO₂CH₃ | 5-OCH₃ | O | H | H | CH₃— | |
| NO₂ | H | O | H | H | H | |
| CO₂CH₃ | H | O | H | H | H | |
| Cl | H | O | H | H | H | |
| SO₂N(CH₃)₂ | H | O | H | H | H | |
| NO₂ | H | O | H | H | OCH₂CH₃ | |
| NO₂ | H | O | H | CH₃ | CH₃ | |
| NO₂ | H | S | H | H | H | |
| CO₂CH₃ | H | O | H | CH₃ | CH₃ | |
| CO₂CH₃ | H | O | H | CH₂CH₃ | CH₃O | |
| CO₂CH₃ | H | O | H | i-C₃H₇ | H | |
| CO₂CH₃ | H | O | CH₃ | H | CH₃ | |
| CO₂CH₃ | H | O | H | H | OCH₂CH₃ | |
| CO₂CH₃ | H | O | H | H | Cl | |
| Cl | H | S | H | H | H | |
| Cl | H | O | CH₃ | H | CH₃O | |
| Cl | H | O | H | H | Cl | |
| Cl | H | O | H | H | OCH₂CH₃ | |

TABLE 4-continued

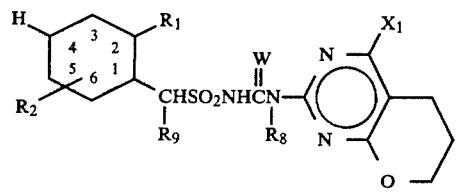

| R₁ | R₂ | W | R₈ | R₉ | X₁ | m.p. (°C.) |
|---|---|---|---|---|---|---|
| CH₃ | H | S | H | H | H | |
| CH₂CH₃ | H | O | H | H | CH₃ | |
| i-C₃H₇ | H | O | H | H | CH₃ | |
| SO₂OCH₂CF₃ | H | O | H | H | CH₃ | |
| OEt | H | O | H | H | CH₃ | |
| O—⟨ | H | O | H | H | CH₃ | |
| CH₂SO₂N(CH₃)₂ | H | O | H | H | CH₃ | |
| CH₂SO₂N(CH₃)—⟨ | H | O | H | H | CH₃ | |
| CH₂SO₂N(CH₃)Et | H | O | H | H | CH₃ | |
| CH₂OCH₃ | H | O | H | H | CH₃ | |
| CH₂OCH₂CH₃ | H | O | H | H | CH₃ | |
| CH₂CO₂CH₃ | H | O | H | H | CH₃ | |
| CH₂CO₂Et | H | O | H | H | CH₃ | |
| OCH₃ | H | O | H | H | CH₃ | |

TABLE 5

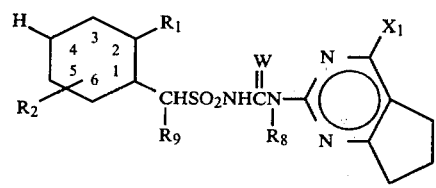

| R₁ | R₂ | W | R₈ | R₉ | X₁ | m.p. (°C.) |
|---|---|---|---|---|---|---|
| NO₂ | H | O | H | H | CH₃ | |
| NO₂ | H | O | H | H | CH₃O | |
| NO₂ | H | O | H | H | OCH₂CH₃ | |
| NO₂ | H | O | H | H | Cl | |
| NO₂ | H | O | CH₃ | H | H | |
| NO₂ | H | S | H | H | CH₃ | |
| NO₂ | H | O | H | CH₃ | CH₃ | |
| CO₂CH₃ | H | O | H | H | CH₃ | |
| CO₂CH₃ | H | O | H | H | CH₃O | |
| CO₂CH₃ | H | O | H | H | OCH₂CH₃ | |
| CO₂CH₃ | H | O | H | H | Cl | |
| CO₂CH₃ | H | O | H | H | H | |
| CO₂CH₃ | H | S | H | H | H | |
| CO₂CH₃ | H | O | H | CH₂CH₃ | CH₃ | |
| CO₂CH₃ | H | O | H | i-C₃H₇ | CH₃ | |
| CO₂CH₃ | H | O | CH₃ | H | H | |
| Cl | H | O | H | H | CH₃ | |
| Cl | H | O | H | H | CH₃O | |
| Cl | H | O | H | H | OCH₂CH₃ | |
| Cl | H | O | H | H | Cl | |
| Cl | H | O | H | H | H | |
| Cl | H | S | H | H | H | |
| Cl | H | O | CH₃ | H | CH₃ | |
| CH₃ | H | O | H | H | CH₃ | |
| CH₃ | H | O | H | H | CH₃O | |
| CH₃ | H | O | H | H | OCH₂CH₃ | |
| CH₂CH₃ | H | O | H | H | Cl | |
| CH₂CH₃ | H | S | H | H | H | |
| i-C₃H₇ | H | O | H | H | CH₃ | |
| SO₂OCH₂CF₃ | H | O | H | H | CH₃ | |
| OEt | H | O | H | H | CH₃ | |

TABLE 5-continued

[Structure: cyclohexane ring with positions labeled 1-6, H at position 4, R1 at position 2, R2 at position 5, with –CH(R9)SO2NHC(=W)N(R8)– linked to a bicyclic pyrimidine bearing X1 and a fused cyclopentane]

| R1 | R2 | W | R8 | R9 | X1 | m.p. (°C.) |
|---|---|---|---|---|---|---|
| O–CH(CH3)2 | H | O | H | H | CH3 | |
| CH2SO2N(CH3)2 | H | O | H | H | CH3 | |
| CH2SO2N(CH3)–CH(CH3)2 | H | O | H | H | CH3 | |
| CH2SO2N(CH3)Et | H | O | H | H | CH3 | |
| CH2OCH3 | H | O | H | H | CH3 | |
| CH2OCH2CH3 | H | O | H | H | CH3 | |
| CH2CO2CH3 | H | O | H | H | CH3 | |
| CH2CO2Et | H | O | H | H | CH3 | |
| OCH3 | H | O | H | H | CH3 | |
| F | H | O | H | H | CH3 | |
| Br | H | O | H | H | CH3 | |
| CO2–CH(CH3)2 | H | O | H | H | CH3 | |
| CO2CH2CH2Cl | H | O | H | H | CH3 | |
| CO2CH2CH=CH2 | H | O | H | H | CH3 | |
| CO2CH2CH2OCH3 | H | O | H | H | CH3 | |
| CH3SO2 | H | O | H | H | CH3 | |
| CF3 | H | O | H | H | CH3 | |
| SO2N(CH3)–OCH3 | H | O | H | H | CH3 | |
| SO2N(CH3)2 | H | O | H | H | CH3 | |
| SO2N(CH3)–C2H5 | H | O | H | H | CH3 | |
| SO2N(CH3)–CH(CH3)2 | H | O | H | H | CH3 | |
| CH3SO2O | H | O | H | H | CH3 | |
| n-C3H7SO2O | H | O | H | H | CH3 | |
| CF3SO2O | H | O | H | H | CH3 | |
| NO2 | 3-Cl | O | H | H | CH3 | |
| NO2 | 5-Cl | O | H | H | CH3 | |
| NO2 | 6-Cl | O | H | H | CH3 | |
| NO2 | 5-Br | O | H | H | CH3 | |
| NO2 | 5-CF3 | O | H | H | CH3 | |
| NO2 | 5-OCH3 | O | H | H | CH3 | |
| CO2CH3 | 5-Cl | O | H | H | CH3 | |
| CO2CH3 | 5-CF3 | O | H | H | CH3 | |
| CO2CH3 | 6-Cl | O | H | H | CH3 | |
| CO2CH3 | 5-Br | O | H | H | CH3 | |
| CO2CH3 | 5-F | O | H | H | CH3 | |
| CO2CH3 | 5-OCH3 | O | H | H | CH3 | |

TABLE 6

| R₁ | R₂ | W | R₈ | R₉ | X₂ | m.p. (°C.) |
|---|---|---|---|---|---|---|
| $NO_2$ | H | O | H | H | $CH_3$ | |
| $NO_2$ | H | O | H | H | $CH_3CH_2-$ | |
| Cl | H | O | H | H | $CH_3$ | |
| Cl | H | O | H | H | $CH_3CH_2-$ | |
| $CO_2CH_3$ | H | O | H | H | $CH_3$ | |
| $CO_2CH_3$ | H | O | H | H | $CH_3CH_2-$ | |
| $CH_3$ | H | O | H | H | $CH_3$ | |
| F | H | O | H | H | $CH_3$ | |
| Br | H | O | H | H | $CH_3$ | |
| $CO_2$-i-Pr | H | O | H | H | $CH_3$ | |
| $CH_3$ | H | O | H | H | $CH_3CH_2-$ | |
| $CO_2CH_2CH_2Cl$ | H | O | H | H | $CH_3$ | |
| $CO_2CH_2CH=CH_2$ | H | O | H | H | $CH_3$ | |
| $CO_2CH_2CH_2OCH_3$ | H | O | H | H | $CH_3$ | |
| $CH_3SO_2$ | H | O | H | H | $CH_3$ | |
| $n-C_3H_7SO_2-$ | H | O | H | H | $CH_3$ | |
| $CF_3SO_2$ | H | O | H | H | $CH_3$ | |
| $CF_3$ | H | O | H | H | $CH_3$ | |
| $SO_2N(CH_3)(OCH_3)$ | H | O | H | H | $CH_3$ | |
| $SO_2N(CH_3)_2$ | H | O | H | H | $CH_3$ | |
| $SO_2N(CH_3)(C_2H_5)$ | H | O | H | H | $CH_3$ | |
| $SO_2N(CH_3)(i-Pr)$ | H | O | H | H | $CH_3-$ | |
| $CH_3SO_2O-$ | H | O | H | H | $CH_3-$ | |
| $n-C_3H_7SO_2O-$ | H | O | H | H | $CH_3-$ | |
| $CF_3SO_2O-$ | H | O | H | H | $CH_3-$ | |
| $NO_2$ | 3-Cl | O | H | H | $CH_3-$ | |
| $NO_2$ | 5-Cl | O | H | H | $CH_3-$ | |
| $NO_2$ | 6-Cl | O | H | H | $CH_3-$ | |
| $NO_2$ | 5-Br | O | H | H | $CH_3-$ | |
| $NO_2$ | 5-$CF_3$ | O | H | H | $CH_3-$ | |
| $NO_2$ | 5-$OCH_3$ | O | H | H | $CH_3-$ | |
| $CO_2CH_3$ | 5-Cl | O | H | H | $CH_3-$ | |
| $CO_2CH_3$ | 5-$CF_3$ | O | H | H | $CH_3-$ | |
| $CO_2CH_3$ | 6-Cl | O | H | H | $CH_3-$ | |
| $CO_2CH_3$ | 5-Br | O | H | H | $CH_3-$ | |
| $CO_2CH_3$ | 5-F | O | H | H | $CH_3-$ | |
| $CO_2CH_3$ | 5-$OCH_3$ | O | H | H | $CH_3-$ | |
| $NO_2$ | H | O | H | H | $CH_3O$ | |
| $NO_2$ | H | O | H | H | $OCH_2CH_3$ | |
| $NO_2$ | H | S | H | H | $CH_3$ | |
| $NO_2$ | H | O | H | $CH_3$ | $CH_2CH_3$ | |
| $CO_2CH_3$ | H | O | $CH_3$ | H | $CH_3$ | |
| $CO_2CH_3$ | H | O | H | $CH_2CH_3$ | $CH_3$ | |
| $CO_2CH_3$ | H | O | H | $i-C_3H_7$ | $CH_3$ | |
| $CO_2CH_3$ | H | S | H | H | $CH_3$ | |
| $CO_2CH_3$ | H | O | H | H | $CH_3O$ | |
| $CO_2CH_3$ | H | O | H | H | $OCH_2CH_3$ | |
| Cl | H | O | H | H | $CH_3O$ | |
| Cl | H | O | H | H | $OCH_2CH_3$ | |
| Cl | H | O | $CH_3$ | H | $CH_3$ | |
| Cl | H | O | H | $CH_3$ | $CH_3$ | |
| $CH_3$ | H | S | H | H | $CH_3$ | |
| $CH_3$ | H | O | H | H | $CH_3O$ | |
| $CH_2CH_3$ | H | O | H | H | $OCH_2CH_3$ | |
| $i-C_3H_7$ | H | O | H | H | $CH_3$ | |

TABLE 6-continued

Structure: cyclohexyl ring (positions 1-6) with H at 4, R₁ at 2, R₂ at 5, and at position 1: —CH(R₉)SO₂NHC(=W)N(R₈)— linked to a pyrido-furan bicyclic system with X₂ substituent and N, N, O ring atoms, with CH₃ on the furan oxygen side.

| R₁ | R₂ | W | R₈ | R₉ | X₂ | m.p. (°C.) |
|---|---|---|---|---|---|---|
| SO₂OCH₂CF₃ | H | O | H | H | CH₃ | |
| OCH₂CH₃ | H | O | H | H | CH₃ | |
| O—CH(CH₃)₂ | H | O | H | H | CH₃ | |
| CH₂SO₂N(CH₃)₂ | H | O | H | H | CH₃ | |
| CH₂SO₂N(CH₃)—CH(CH₃)₂ | H | O | H | H | CH₃ | |
| CH₂SO₂N(CH₃)Et | H | O | H | H | CH₃ | |
| CH₂OCH₃ | H | O | H | H | CH₃ | |
| CH₂OCH₂CH₃ | H | O | H | H | CH₃ | |
| CH₂CO₂CH₃ | H | O | H | H | CH₃ | |
| CH₂CO₂Et | H | O | H | H | CH₃ | |
| OCH₃ | H | O | H | H | CH₃ | |

TABLE 7

Structure: cyclohexyl ring with H at 4, R₁ at 2, R₂ at 5, and at position 1: —CH(R₉)SO₂NHC(=W)N(R₈)— linked to a pyrimidine with X₃ and Y₁ substituents.

| R₁ | R₂ | W | R₈ | R₉ | X₃ | Y₁ | m.p. (°C.) |
|---|---|---|---|---|---|---|---|
| NO₂ | H | O | H | H | CH₃O | CH₃O | |
| NO₂ | H | O | H | H | CH₃O | CH₃ | |
| NO₂ | H | O | H | H | CH₃ | CH₃ | |
| NO₂ | H | S | H | H | CH₃O | CH₃ | |
| NO₂ | H | O | CH₃ | H | CH₃O | CH₃ | |
| NO₂ | H | O | H | CH₃ | CH₃O | CH₃ | |
| Cl | H | O | H | H | CH₃O | CH₃O | |
| Cl | H | O | H | H | CH₃O | CH₃ | |
| Cl | H | O | H | H | CH₃ | CH₃ | |
| Cl | H | S | H | H | CH₃O | CH₃ | |
| Cl | H | O | CH₃ | H | CH₃O | CH₃ | |
| CO₂CH₃ | H | O | H | H | CH₃O | CH₃O | |
| CO₂CH₃ | H | O | H | H | CH₃O | CH₃ | |
| CO₂CH₃ | H | O | H | H | CH₃ | CH₃ | |
| CO₂CH₃ | H | S | H | H | CH₃O | CH₃ | |
| CO₂CH₃ | H | O | CH₃ | H | CH₃O | CH₃ | |
| CO₂CH₃ | H | O | H | CH₂CH₃ | CH₃O | CH₃ | |
| CO₂CH₃ | H | O | H | i-C₃H₇ | CH₃O | CH₃ | |
| CH₃ | H | O | H | H | CH₃O | CH₃O | |
| CH₃ | H | O | H | H | CH₃O | CH₃ | |
| CH₃ | H | O | H | H | CH₃ | CH₃ | |
| CH₃ | H | S | H | H | CH₃O | CH₃ | |
| CH₃ | H | O | CH₃ | H | CH₃O | CH₃ | |
| CH₃ | H | O | H | CH₃ | CH₃O | CH₃ | |
| F | H | O | H | H | CH₃O | CH₃ | |
| Br | H | O | H | H | CH₃O | CH₃ | |
| CH₃O | H | O | H | H | CH₃O | CH₃O | |
| CO₂—CH(CH₃)₂ | H | O | H | H | CH₃O | CH₃O | |
| CO₂CH₂CH₂Cl | H | O | H | H | CH₃O | CH₃O | |
| CO₂CH₂CH=CH₂ | H | O | H | H | CH₃O | CH₃O | |
| CO₂CH₂CH₂OCH₃ | H | O | H | H | CH₃O | CH₃O | |
| CH₃SO₂ | H | O | H | H | CH₃O | CH₃O | |
| n-C₃H₇SO₂ | H | O | H | H | CH₃O | CH₃O | |
| CF₃SO₂ | H | O | H | H | CH₃O | CH₃O | |

TABLE 7-continued

Structure: cyclohexane with H at position 4, R₁ at position 2, R₂ at position 5, CHSO₂NHC(=W)N(R₈)- connected to pyrimidine with X₃ and Y₁ substituents; R₉ on the CH.

| R₁ | R₂ | W | R₈ | R₉ | X₃ | Y₁ | m.p. (°C) |
|---|---|---|---|---|---|---|---|
| CF₃ | H | O | H | H | CH₃O | CH₃O | |
| SO₂N(OCH₃)CH₃ | H | O | H | H | CH₃O | CH₃O | |
| SO₂N(CH₃)₂ | H | O | H | H | CH₃O | CH₃O | |
| SO₂N(CH₃)CH₂CH₃ | H | O | H | H | CH₃O | CH₃O | |
| SO₂N(CH₃)-i-Pr | H | O | H | H | CH₃O | CH₃O | |
| CH₃SO₂O | H | O | H | H | CH₃O | CH₃O | |
| n-C₃H₇SO₂O | H | O | H | H | CH₃O | CH₃O | |
| CF₃SO₂O | H | O | H | H | CH₃O | CH₃O | |
| NO₂ | 3-Cl | O | H | H | CH₃O | CH₃O | |
| NO₂ | 5-Cl | O | H | H | CH₃O | CH₃O | |
| NO₂ | 6-Cl | O | H | H | CH₃O | CH₃O | |
| NO₂ | 5-Br | O | H | H | CH₃O | CH₃O | |
| NO₂ | 5-F | O | H | H | CH₃O | CH₃O | |
| NO₂ | 5-CF₃ | O | H | H | CH₃O | CH₃O | |
| NO₂ | 5-OCH₃ | O | H | H | CH₃O | CH₃O | |
| CO₂CH₃ | 5-Cl | O | H | H | CH₃O | CH₃ | |
| CO₂CH₃ | 5-CF₃ | O | H | H | CH₃O | CH₃O | |
| CO₂CH₃ | 6-Cl | O | H | H | CH₃O | CH₃O | |
| CO₂CH₃ | 5-Br | O | H | H | CH₃O | CH₃O | |
| CO₂CH₃ | 5-F | O | H | H | CH₃O | CH₃O | |
| CO₂CH₃ | 5-OCH₃ | O | H | H | CH₃O | CH₃O | |
| CH₂CH₃ | H | O | H | H | CH₃O | CH₃O | |
| i-C₃H₇ | H | O | H | H | CH₃O | CH₃O | |
| SO₂OCH₂CF₃ | H | O | H | H | CH₃O | CH₃O | |
| OCH₂CH₃ | H | O | H | H | CH₃O | CH₃O | |
| O-i-Pr | H | O | H | H | CH₃O | CH₃O | |
| CH₂SO₂N(CH₃)₂ | H | O | H | H | CH₃O | CH₃O | |
| CH₂SO₂N(CH₃)-i-Pr | H | O | H | H | CH₃O | CH₃O | |
| CH₂SO₂N(CH₃)Et | H | O | H | H | CH₃O | CH₃O | |
| CH₂OCH₃ | H | O | H | H | CH₃O | CH₃O | |
| CH₂OCH₂CH₃ | H | O | H | H | CH₃O | CH₃O | |
| CH₂CO₂CH₃ | H | O | H | H | CH₃O | CH₃O | |
| CH₂CO₂Et | H | O | H | H | CH₃O | CH₃O | |

TABLE 8

Structure: cyclohexane with H at position 4, R₁ at position 2, R₂ at position 5, CHSO₂NHC(=W)N(R₈)- connected to triazine (N-N, N) with X₃ and Y₁ substituents; R₉ on the CH.

| R₁ | R₂ | W | R₈ | R₉ | X₃ | Y₁ | m.p. (°C) |
|---|---|---|---|---|---|---|---|
| NO₂ | H | O | H | H | CH₃O | CH₃O | |
| NO₂ | H | O | H | H | CH₃O | CH₃ | |
| NO₂ | H | O | H | H | CH₃ | CH₃ | |
| NO₂ | H | S | H | H | CH₃O | CH₃ | |

TABLE 8-continued

| R₁ | R₂ | W | R₈ | R₉ | X₃ | Y₁ | m.p. (°C.) |
|---|---|---|---|---|---|---|---|
| NO₂ | H | O | CH₃ | H | CH₃O | CH₃ | |
| NO₂ | H | O | H | CH₃ | CH₃O | CH₃ | |
| Cl | H | O | H | H | CH₃O | CH₃O | |
| Cl | H | O | H | H | CH₃O | CH₃ | |
| Cl | H | O | H | H | CH₃ | CH₃ | |
| Cl | H | S | H | H | CH₃O | CH₃ | |
| Cl | H | O | CH₃ | H | CH₃O | CH₃ | |
| CO₂CH₃ | H | O | H | H | CH₃O | CH₃O | |
| CO₂CH₃ | H | O | H | H | CH₃O | CH₃ | |
| CO₂CH₃ | H | O | H | H | CH₃ | CH₃ | |
| CO₂CH₃ | H | S | H | H | CH₃O | CH₃ | |
| CO₂CH₃ | H | O | CH₃ | H | CH₃O | CH₃ | |
| CO₂CH₃ | H | O | H | CH₂CH₃ | CH₃O | CH₃ | |
| CO₂CH₃ | H | O | H | i-C₃H₇ | CH₃O | CH₃ | |
| CH₃ | H | O | H | H | CH₃O | CH₃O | |
| CH₃ | H | O | H | H | CH₃O | CH₃ | |
| CH₃ | H | O | H | H | CH₃ | CH₃ | |
| CH₃ | H | S | H | H | CH₃O | CH₃ | |
| CH₃ | H | O | CH₃ | H | CH₃O | CH₃ | |
| CH₃ | H | O | H | CH₃ | CH₃O | CH₃ | |
| F | H | O | H | H | CH₃O | CH₃ | |
| Br | H | O | H | H | CH₃O | CH₃ | |
| CH₃O | H | O | H | H | CH₃O | CH₃O | |
| CO₂—⟨ | H | O | H | H | CH₃O | CH₃O | |
| CO₂CH₂CH₂Cl | H | O | H | H | CH₃O | CH₃O | |
| CO₂CH₂CH=CH₂ | H | O | H | H | CH₃O | CH₃O | |
| CO₂CH₂CH₂OCH₃ | H | O | H | H | CH₃O | CH₃O | |
| CH₃SO₂ | H | O | H | H | CH₃O | CH₃O | |
| n-C₃H₇SO₂ | H | O | H | H | CH₃O | CH₃O | |
| CF₃SO₂ | H | O | H | H | CH₃O | CH₃O | |
| CF₃ | H | O | H | H | CH₃O | CH₃O | |
| SO₂N(OCH₃)CH₃ | H | O | H | H | CH₃O | CH₃O | |
| SO₂N(CH₃) | H | O | H | H | CH₃O | CH₃O | |
| SO₂N(CH₃)CH₂CH₃ | H | O | H | H | CH₃O | CH₃O | |
| SO₂N(CH₃)—⟨ | H | O | H | H | CH₃O | CH₃O | |
| CH₃SO₂O | H | O | H | H | CH₃O | CH₃O | |
| n-C₃H₇SO₂O | H | O | H | H | CH₃O | CH₃O | |
| CF₃SO₂O | H | O | H | H | CH₃O | CH₃O | |
| NO₂ | 3-Cl | O | H | H | CH₃O | CH₃O | |
| NO₂ | 5-Cl | O | H | H | CH₃O | CH₃O | |
| NO₂ | 6-Cl | O | H | H | CH₃O | CH₃O | |
| NO₂ | 5-Br | O | H | H | CH₃O | CH₃O | |
| NO₂ | 5-F | O | H | H | CH₃O | CH₃O | |
| NO₂ | 5-CF₃ | O | H | H | CH₃O | CH₃O | |
| NO₂ | 5-OCH₃ | O | H | H | CH₃O | CH₃O | |
| CO₂CH₃ | 5-Cl | O | H | H | CH₃O | CH₃ | |
| CO₂CH₃ | 5-CF₃ | O | H | H | CH₃O | CH₃O | |
| CO₂CH₃ | 6-Cl | O | H | H | CH₃O | CH₃O | |
| CO₂CH₃ | 5-Br | O | H | H | CH₃O | CH₃O | |
| CO₂CH₃ | 5-F | O | H | H | CH₃O | CH₃O | |
| CO₂CH₃ | 5-OCH₃ | O | H | H | CH₃O | CH₃O | |
| CH₂CH₃ | H | O | H | H | CH₃O | CH₃O | |
| i-C₃H₇ | H | O | H | H | CH₃O | CH₃O | |
| SO₂OCH₂CF₃ | H | O | H | H | CH₃O | CH₃O | |
| OCH₂CH₃ | H | O | H | H | CH₃O | CH₃O | |

TABLE 8-continued

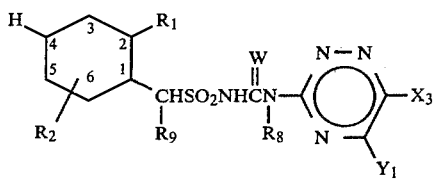

| R₁ | R₂ | W | R₈ | R₉ | X₃ | Y₁ | m.p. (°C.) |
|---|---|---|---|---|---|---|---|
| O—< | H | O | H | H | CH₃O | CH₃O | |
| CH₂SO₂N(CH₃)₂ | H | O | H | H | CH₃O | CH₃O | |
| CH₂SO₂N(CH₃)—< | H | O | H | H | CH₃O | CH₃O | |
| CH₂SO₂N(CH₃)Et | H | O | H | H | CH₃O | CH₃O | |
| CH₂OCH₃ | H | O | H | H | CH₃O | CH₃O | |
| CH₂OCH₂CH₃ | H | O | H | H | CH₃O | CH₃O | |
| CH₂CO₂CH₃ | H | O | H | H | CH₃O | CH₃O | |
| CH₂CO₂Et | H | O | H | H | CH₃O | CH₃O | |

TABLE 9

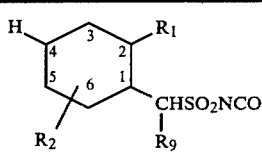

| R₁ | R₂ | R₉ | IR SO₂NCO |
|---|---|---|---|
| NO₂ | H | H | 2230 cm⁻¹ |
| Cl | H | H | 2240 cm⁻¹ |
| CO₂CH₃ | H | H | 2230 cm⁻¹ |
| CH₃ | H | H | 2250 cm⁻¹ |
| F | H | H | |
| Br | H | H | |
| CO₂—< | H | H | |
| CH₃SO₂ | H | H | 2240 cm⁻¹ |
| CF₃SO₂ | H | H | |
| CF₃ | H | H | |
| SO₂N(CH₃)₂ | H | H | 2240 cm⁻¹ |
| SO₂N(CH₃)OCH₃ | H | H | |
| CH₃SO₂O— | H | H | 2240 cm⁻¹ |
| CF₃SO₂O— | H | H | |
| NO₂ | 3-Cl | H | |
| NO₂ | 5-Cl | H | |
| NO₂ | 6-Cl | H | |
| NO₂ | 5-Br | H | |
| NO₂ | 5-CF₃ | H | |
| NO₂ | 5-OCH₃ | H | |
| NO₂ | H | CH₃ | 2240 cm⁻¹ |
| CO₂CH₃ | H | CH₃ | |
| CO₂CH₃ | H | CH₂CH₃ | |
| CO₂CH₃ | H | i-C₃H₇ | |
| Cl | H | CH₃ | |
| CH₃ | H | CH₃ | |
| CH₂CH₃ | H | H | |
| i-C₃H₇ | H | H | |
| SO₂OCH₂CF₃ | H | H | |
| OCH₂CH₃ | H | H | |
| O—< | H | H | |

TABLE 9-continued

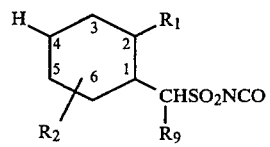

| R₁ | R₂ | R₉ | IR SO₂NCO |
|---|---|---|---|
| CH₂SO₂N(CH₃)₂ | H | H | |
| CH₂SO₂N(CH₃)—< | H | H | |
| CH₂SO₂N(CH₃)Et | H | H | |
| CH₂OCH₃ | H | H | |
| CH₂OCH₂CH₃ | H | H | |
| CH₂CO₂CH₃ | H | H | |
| CH₂CO₂Et | H | H | |
| OCH₃ | H | H | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 10

| Active Ingredient | Weight Percent | |
|---|---|---|
| | Diluent(s) | Surfactant(s) |
| Wettable Powders | 20-90 | 0-74 | 1-10 |
| Oil Suspensions, | 3-50 | 40-95 | 0-15 |

TABLE 10-continued

| | Active Ingredient | Weight Percent | |
|---|---|---|---|
| | | Diluent(s) | Surfactant(s) |
| Emulsions, Solutions (including Emulsifiable Concentrates) | | | |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, December 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,233,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 17

| Wettable Powder | |
|---|---|
| N—[(4,6-dimethoxypyrimidin-2-yl)aminocarbonyl]-1-(2-nitrophenyl)methanesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 18

| Wettable Powder | |
|---|---|
| N—[(4,6-dimethoxy-1,3,5-triazin-2-yl)aminocarbonyl]-1-(2-nitrophenyl)methanesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 19

| Granule | |
|---|---|
| Wettable Powder of Example 18 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 20

| Extruded Pellet | |
|---|---|
| N—[(4-methoxy-6-methylpyrimidin-2-yl)aminocarbonyl]-1-(2-nitrophenyl)methanesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 21

| Oil Suspension | |
|---|---|
| N—[(4-methoxy-6-methyl-1,3,5-triazin-2-yl)aminocar- | 25% |

-continued

| Oil Suspension | |
|---|---|
| bonyl]-1-(2- nitrophenyl)methanesulfonamide | |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 22

| Wettable Powder | |
|---|---|
| N—[(4,6-dimethylpyrimidin-2-yl)aminocarbonyl]-1-(2-nitrophenyl)methanesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 23

| Low Strength Granule | |
|---|---|
| 2-[[(4,6-dimethoxypyrimidin-2-yl)aminocarbonyl]aminosulfonylmethyl]benzoic acid, methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 24

| Aqueous Suspension | |
|---|---|
| N—[(4,6-dimethoxypyrimidin-2-yl)aminocarbonyl]-1-(2-methylsulfonyloxyphenyl)methanesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 25

| Solution | |
|---|---|
| 2-[[(4,6-dimethoxy-1,3,5-triazin-2-yl)aminocarbonyl]aminosulfonylmethyl]benzoic acid, methyl ester | 5% |
| water | 95% |

The salt is added directly to the water with stirring to produce the solution, which may then be packaged for use.

EXAMPLE 26

| Low Strength Granule | |
|---|---|
| 2-[[(4,6-dimethyl-1,3,5-triazin-2-yl)aminocarbonyl]-aminosulfonylmethyl]benzoic acid, methyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 27

| Granule | |
|---|---|
| N—[(4,6-dimethylpyzimidin-2-yl)aminocarbonyl]-1 (2-nitrophenyl)methanesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 28

| High Strength Concentrate | |
|---|---|
| N—[(4,6-dimethoxypyrimidin-2-yl)aminocarbonyl]-1-(2-nitrophenyl)methanesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 29

| Wettable Powder | |
|---|---|
| N—[(4,6-dimethoxy-1,3,5-triazin-2-yl)aminocarbonyl]-1-(2-nitrophenyl)methanesulfonamide | 90% |
| dioctyl sodium sulfoccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 30

| Wettable Powder | |
|---|---|
| 2-[[(4-methoxy-6-methylpyrimidin-2-yl)aminocarbonyl]-aminosulfonylmethyl]bwnzoic acid methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 31

| Oil Suspension | |
|---|---|
| 2-[[(4,6-dimethylpyrimidin-2-yl)aminocarbonyl]aminosulfonylmethyl]benzoic acid, methyl ester | 35% |
| blend of polyalcohol carboxylic esters and oil soluble petroleum sulfonates | 6% |
| xylenes | 59% |

The ingredients are combined and ground together in a sand mill to produce particles essentially all below 5 microns. The product can be used directly, extended with oils, or emulsified in water.

EXAMPLE 32

| Dust | |
|---|---|
| 2-[[(4-methoxy-6-methyl-1,3,5-triazin-2-yl)aminocarbonyl]aminosulfonylmethyl]benzoic acid, methyl ester | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

The compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures or under perimeter fences. Alternatively, the subject compounds are useful for the selective pre- or post-emergence weed control in crops, such as wheat, barley, corn, rice and soybeans.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for selective weed control or for situations where only short-term persistence is required.

The compounds of the invention may be used in combination with any other herbicides, examples of which are those of the triazine, triazole, uracil, urea, amide, diphenylether, carbamate and bipyridylium types. Especially useful are combinations of the compounds of this invention with S-(4-chlorobenzyl)-N,N-diethylthiolcarbamate; 2-chloro-2',6'-diethyl-N-(butoxymethyl)acetanilide; S-ethyl-N,N-hexamethylenethiolcarbamate; 1-$\alpha,\alpha$-dimethylbenzyl-3-p-tolylurea; 1-($\alpha,\alpha$-dimethylbenzyl)-3-methyl-3-phenylurea; 2,4-dichlorophenyl-3-methoxy-4-nitrophenyl ether; 2,4,6-trichlorophenyl-4'-nitrophenyl ether; 4-(2,4-dichlorobenzoyl)-1,3-dimethyl-5-pyrazolyl-p-toluenesulfonate; O-ethyl-O-(3-methyl-6-nitrophenol)-N-sec-butyl phosphoramid-thioate; S-(1-methyl-1-phenethyl)piperidine-1-carbathioate; 2-chloro-2',6'-diethyl-N-(N-propoxyethyl)acetanilide; 4-ethoxymethoxybenz-2',3'-dichloranilide; 2-benzthiazol-2-iloxy-N-methylacetoanilide; 5-t-butyl-3-(2,4-dichloro-5-isopropoxyphenyl)-1,3,4-oxadiazol-2-one; 3',4'-dichloropropionanilide; and N-(1-ethylpropyl)-2,6-dinitro-3,4-xylidine.

The herbicidal properties of the subject compounds were discovered in a number of greenhouse tests. The test procedures and results follow.

TEST A

Seeds of crabgrass (*Digitaria sp.*), barnyardgrass (*Echinochloa crusgalli*), wild oats (*Avena fatua*), cassia (*Cassia tora*), morningglory (*Ipomoea sp.*), cocklebur (*Xanthium sp.*), sorghum, corn, soybean, rice, wheat and nutsedge tubers (*Cyperus rotundus*) were planted in a growth medium and treated preemergence with the chemicals dissolved in a non-phytotoxic solvent. At the same time, cotton having five leaves (including cotyledonary ones), bush beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings:

C=chlorosis/necrosis;
D=defoliation;
E=emergence inhibition;
G=growth retardation;
H=formative effects;
S=albinism;
U=unusual pigmentation; and
6Y=abscised buds or flowers.

The ratings for the compounds tested by this procedure are presented in Table A. It will be seen that certain of the compounds tested have utility for selective weed control in corn, rice and wheat.

Structures
Compound 1
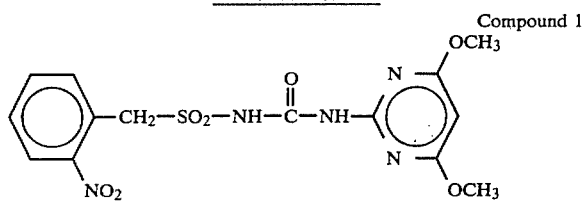
Compound 2
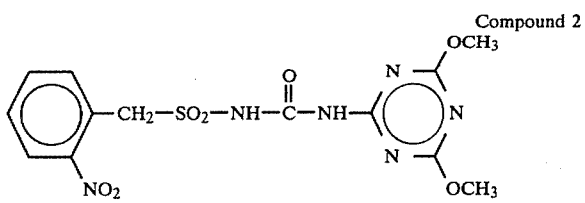
Compound 3
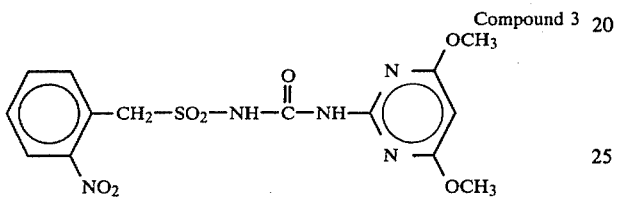
Compound 4
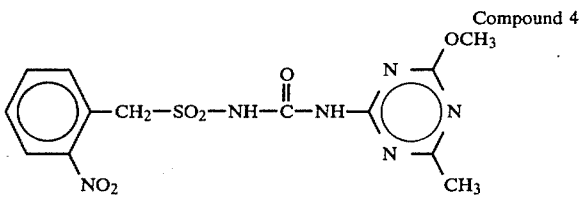
Compound 5
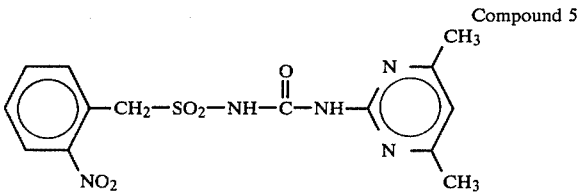
Compound 6
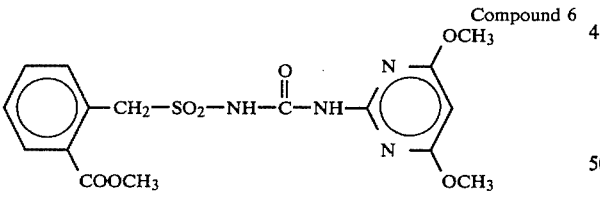
Compound 7
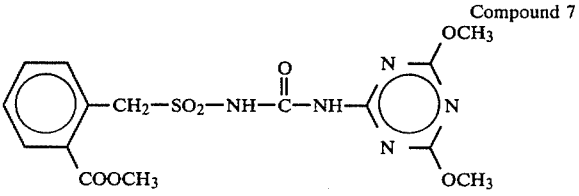
Compound 8
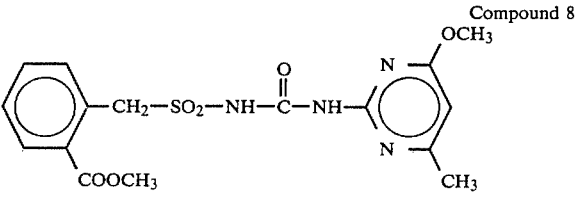
-continued
Structures
Compound 9
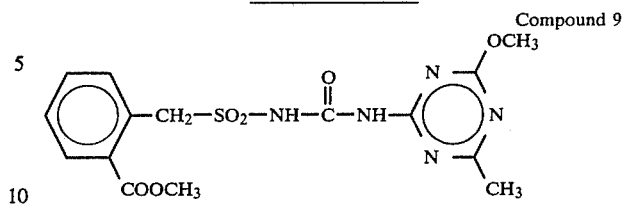
Compound 10
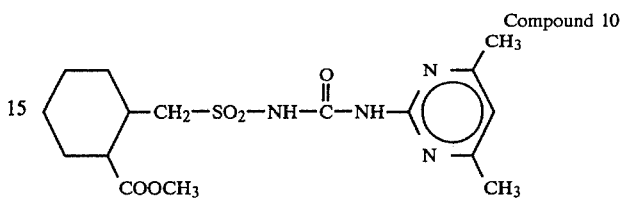
Compound 11
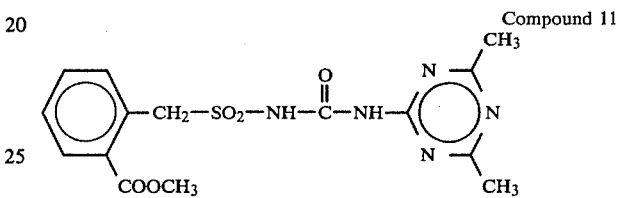
Compound 12
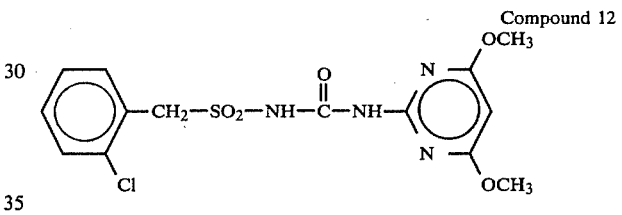
Compound 13
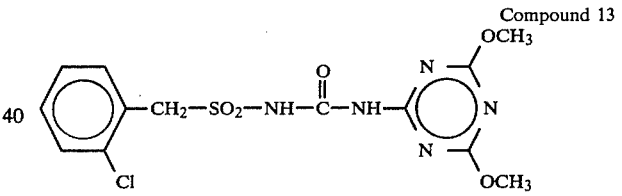
Compound 14
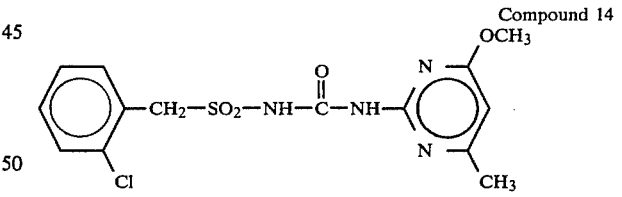
Compound 15
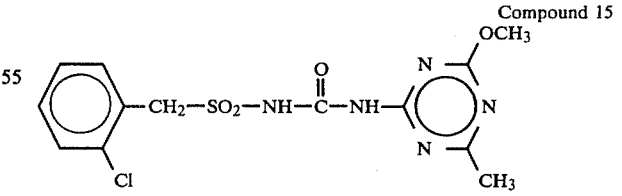
Compound 16
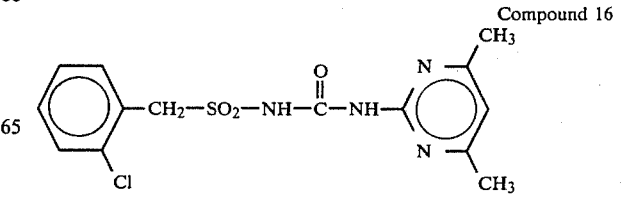

-continued
Structures
Compound 17
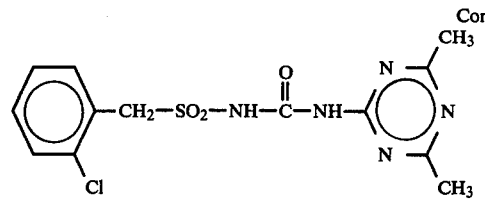
Compound 18
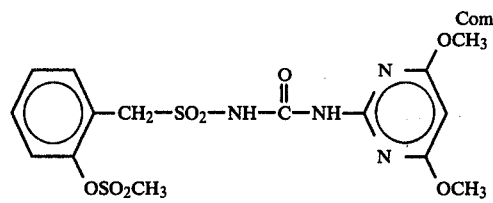
Compound 19
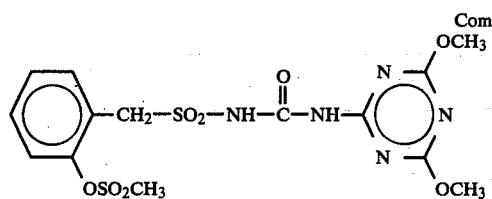
Compound 20
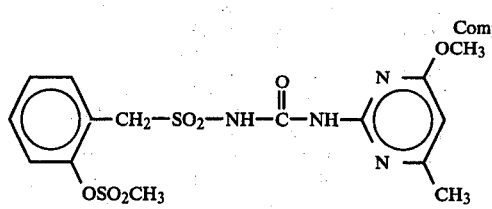
Compound 21
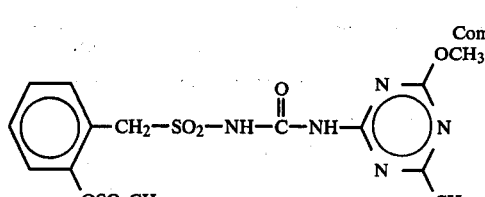
Compound 22
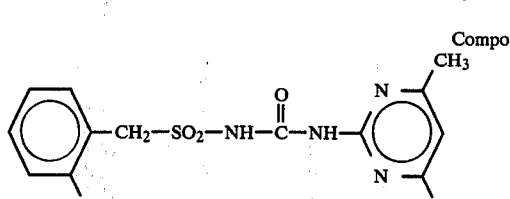
Compound 23
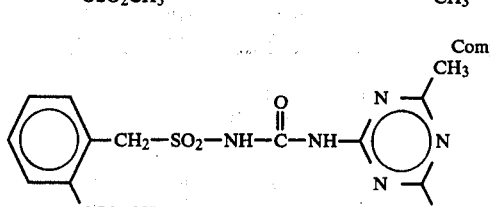
Compound 24
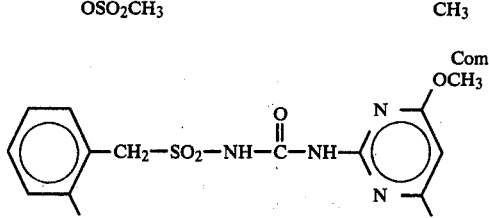
-continued
Structures
Compound 25
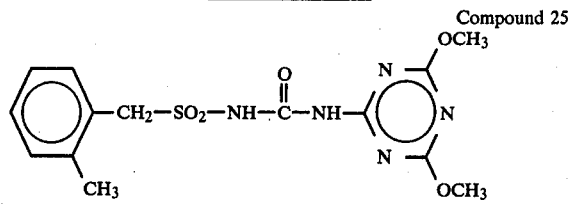
Compound 26
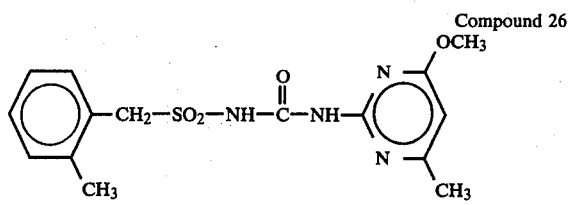
Compound 27
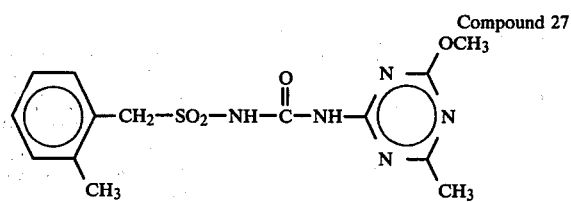
Compound 28
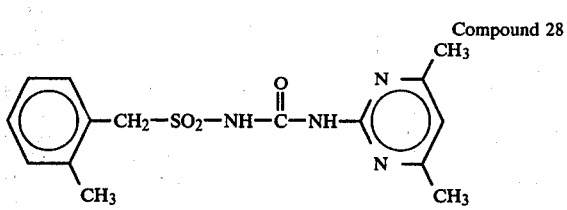
Compound 29
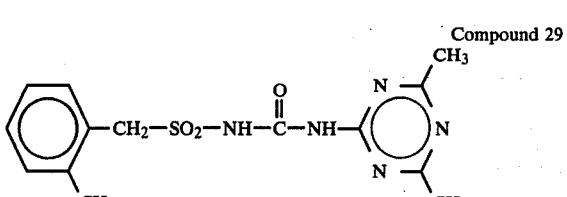
Compound 30
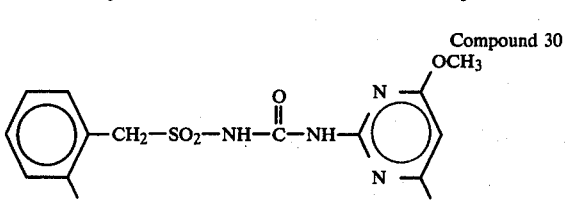
Compound 31
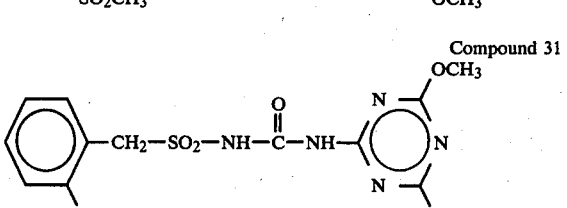
Compound 32
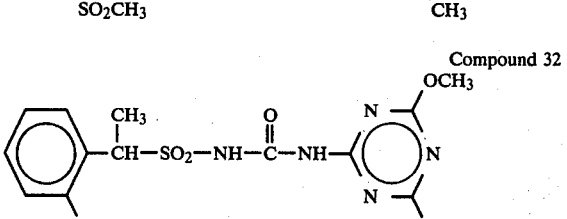

-continued
Structures

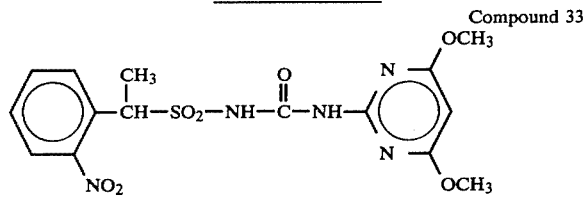

Compound 33

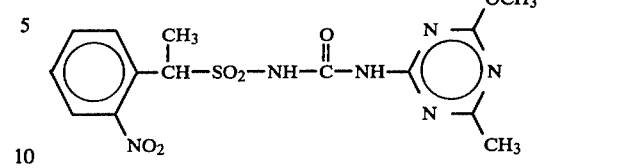

Compound 35

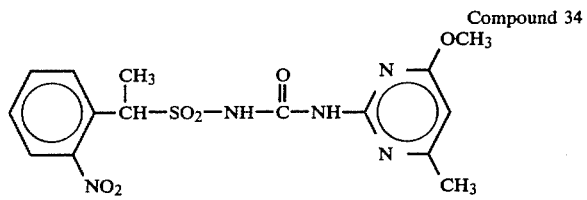

Compound 34

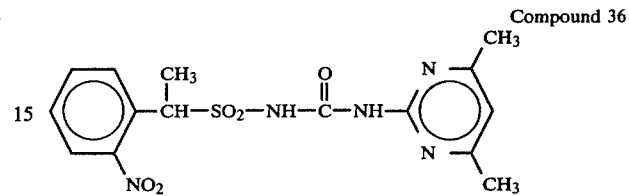

Compound 36

TABLE A

| Rate kg/ha | Cmpd. 1<br>0.4 | Cmpd. 2<br>0.4 | Cmpd. 3<br>0.4 | Cmpd. 4<br>0.4 | Cmpd. 5<br>0.4 | Cmpd. 6<br>0.4 | Cmpd. 7<br>0.4 | Cmpd. 8<br>0.4 | Cmpd. 9<br>0.4 |
|---|---|---|---|---|---|---|---|---|---|
| | | | | POST-EMERGENCE | | | | | |
| Bush bean | 7C,9G,6Y | 5C,9G,6Y | 5C,9G,6Y | 9D,9G,6Y | 3C,9G,6Y | 9C | 9C | 6C,9G | 9C |
| Cotton | 6C,9G | 6C,9G | 3C,3H,8G | 6C,9G | 2C,2H,7G | 6C,9G | 6C,9G | 7C,9G | 9C |
| Morningglory | 10C | 5C,9G | 9C | 10C | 2C,9H | 10C | 10C | 5C,9G | 10C |
| Cocklebur | 3C,9G | 4G | 9C | 9C | 3C,9G | 2C,8G | 9C | 9C | 10C |
| Cassia | 1C,9G | 1C,2H | 3C,7G | 2C,4G | 1C | 6C,9G | 6C,9G | 5C,9G | 9C |
| Nutsedge | 4C,9G | 1C,7G | 9G | 2C,8G | 0 | 9C | 6C,9G | 1C,8G | 2C,9H |
| Crabgrass | 2G | 2C,7G | 1H | 2C,8G | 0 | 4C,8G | 5C,9G | 4G | 9C |
| Barnyardgrass | 3G | 2C,5H | 2C,8H | 3C,9H | 0 | 2C,6G | 5C,9H | 2C,9H | 9C |
| Wild Oats | 0 | 3G | 0 | 2C,3G | 0 | 2G | 1C,9G | 1C,6G | 2C,7G |
| Wheat | 0 | 2G | 0 | 2C,3G | 0 | 4G | 1C,9G | 4G | 2C,9G |
| Corn | 0 | 9G | 2C,9H | 3C,9G | 2C,5H | 1C,8H | 5C,9G | 2C,9H | 5U,9G |
| Soybean | 2C,9G | 2C,9G | 3C,9G | 3C,9G | 1C,4H | 5C,9G | 9C | 3C,9H | 5C,9G |
| Rice | 1C | 3C,9G | 8G | 2C,9G | 2G | 5G | 5C,9G | 1C,8G | 5C,9G |
| Sorghum | 1C,5G | 1C,9G | 9G | 10C | 2C,8H | 2C,8G | 9C | 9G | 9C |

| Rate kg/ha | Cmpd. 10<br>0.4 | Cmpd. 11<br>0.4 | Cmpd. 12<br>0.4 | Cmpd. 13<br>0.4 | Cmpd. 14<br>0.4 | Cmpd. 15<br>0.4 | Cmpd. 16<br>0.4 | Cmpd. 17<br>0.4 | Cmpd. 18<br>0.4 |
|---|---|---|---|---|---|---|---|---|---|
| | | | | POST-EMERGENCE | | | | | |
| Bush bean | 9D,9G,6Y | 4C,9G,6Y | 3C,5G,6Y | 5C,8G,6Y | 4S,8G,6Y | 5S,9G,6Y | 0 | 0 | 9C |
| Cotton | 5C,9G | 6C,9G | 3C,2H,5G | 5C,9G | 3C,3H,5G | 5C,9G | 0 | 1C,3H | 9C |
| Morningglory | 10C | 5C,9G | 3C,7G | 4C,9G | 3C,8G | 3C,9G | 0 | 0 | 10C |
| Cocklebur | 3C,9H | 4C,9G | 1C,4G | 3G | 3C,8H | 3C,9G | 0 | 0 | 3C,9G |
| Cassia | 3C,4H | 5C | 1C | 3C | 2C | 3C | 0 | 0 | 3C,7G |
| Nutsedge | 7G | 1C,6G | 4G | 1C | 3C,9G | 0 | 0 | 0 | 9C |
| Crabgrass | 1C,3H | 1C,5G | 1C | 2G | 0 | 1C,3G | 0 | 0 | 9C |
| Barnyardgrass | 3C,8H | 9H | 0 | 3G | 0 | 3C,9H | 0 | 0 | 6C,9H |
| Wild Oats | 2G | 0 | 0 | 0 | 0 | 0 | 0 | 0 | 7G |
| Wheat | 2G | 0 | 0 | 0 | 0 | 3G | 0 | 0 | 2C,8G |
| Corn | 5C,9H | 3C,9H | 0 | 1C,4G | 1C,3H | 2C,7H | 0 | 0 | 3U,9G |
| Soybean | 3C,9G | 2C,7G | 1C,2H | 2C,4H | 1C,3H | 1C,3H | 0 | 1C,6G | 6C,9H |
| Rice | 2C,8G | 2C,8G | 0 | 1C,6G | 3G | 1C,6G | 0 | 0 | 2C,6G |
| Sorghum | 3C,9H | 2C,9G | 0 | 2C,8H | 1C,3G | 2C,9H | 0 | 0 | 2C,9G |

| Rate kg/ha | Cmpd. 19<br>0.4 | Cmpd. 20<br>0.4 | Cmpd. 21<br>0.4 | Cmpd. 22<br>0.4 | Cmpd. 23<br>0.4 | Cmpd. 24<br>0.4 | Cmpd. 25<br>0.4 | Cmpd. 26<br>0.4 | Cmpd. 27<br>0.4 | Cmpd. 28<br>0.4 | Cmpd. 29<br>0.4 |
|---|---|---|---|---|---|---|---|---|---|---|---|
| | | | | | POST-EMERGENCE | | | | | | |
| Bush bean | 5C,9G | 6C,9G | 9C | 3C,9G,6Y | 4S,8G,6Y | 1C | 1C | 0 | 2C,6F | 1C | 2C,5G |
| Cotton | 6C,9G | 6C,9G | 6C,9G | 6C,9G | 2C,2H | 0 | 2C,2H | 2C,4G | 2C,2H | 1C | 1C,2G |
| Morningglory | 5C,9G | 4C,9G | 4C,9G | 2C,7G | 2C,5H | 0 | 2C,7H | 2C,2H | 4C,9G | 1C | 2C |
| Cocklebur | 4G | 6C,9G | 9C | 3C,9G | 3C | 0 | 0 | 0 | 3C,7G | 1C | 1C,5G |
| Cassia | 2C,3G | 3C,3H | 4C,3H | 3C | 2C | 0 | 2C | 0 | 3C | 0 | 5G |
| Nutsedge | 9G | 2C,8G | 2C,8G | 1C,9G | 3C,8G | 0 | 0 | 0 | 2G | 0 | 1C |
| Crabgrass | 5C,8G | 3C,8G | 6C,9G | 1C,4G | 3C,8G | 0 | 1C,7G | 0 | 2C,5G | 0 | 0 |
| Barnyardgrass | 3C,9H | 2C,9H | 5C,9H | 3C,8H | 4C,9H | 0 | 1C,5H | 0 | 3C,8H | 0 | 0 |
| Wild Oats | 3C,8G | 2C,8G | 9G | 4G | 1C,9G | 0 | 0 | 0 | 0 | 0 | 0 |
| Wheat | 4C,8G | 4C,7G | 3C,9G | 4G | 2C,9G | 0 | 0 | 0 | 8G | 0 | 0 |
| Corn | 8U,9C | 2U,9G | 8U,9G | 2C,8G | 2C,8G | 0 | 1C,6H | 0 | 2C,7H | 0 | 0 |
| Soybean | 4C,9G | 9C | 5C,9G | 2C,9G | 2C,2H | 0 | 2C | 0 | 1C,1H | 1C | 1C |
| Rice | 5C,9G | 4C,8G | 4C,9G | 2C,7C | 4C,7G | 0 | 1C,5G | 0 | 2C,7G | 0 | 0 |
| Sorghum | 9C | 3C,9G | 9C | 2C,9G | 3C,9G | 0 | 2C,9G | 0 | 9G | 0 | 0 |

| | Cmpd. 30<br>0.4 | Cmpd. 31<br>0.4 | Cmpd. 32<br>0.4 | Cmpd. 33<br>0.4 | Cmpd. 34<br>0.4 | Cmpd. 35<br>0.4 | Cmpd. 36<br>0.4 |
|---|---|---|---|---|---|---|---|
| Rate kg/ha | | | | | | | |
| | | | | POST-EMERGENCE | | | |

TABLE A-continued

|  | | | | | | | | |
|---|---|---|---|---|---|---|---|---|
| Bush bean | 9C | 5C,9G,6Y | 1C | 0 | 0 | 0 | 0 | 0 |
| Cotton | 9C | 5C,8G | 0 | 1C | 0 | 0 | 0 | 0 |
| Morningglory | 10C | 4C,8H | 1C | 0 | 0 | 0 | 0 | 0 |
| Cocklebur | 9C | 4C,9G | 0 | 1C,6H | 0 | 0 | 0 | 0 |
| Cassia | 9C | 4C,6H | 0 | 0 | 0 | 0 | 0 | 0 |
| Nutsedge | 9C | 9C | 0 | 0 | 0 | 0 | 0 | 0 |
| Crabgrass | 9C | 9C | 2G | 0 | 0 | 0 | 0 | 0 |
| Barnyardgrass | 9C | 9C | 0 | 0 | 0 | 0 | 0 | 0 |
| Wild Oats | 2C,9C | 0 | 2G | 0 | 0 | 0 | 0 | 0 |
| Wheat | 3C,9G | 5U,9G | 0 | 0 | 0 | 0 | 0 | 0 |
| Corn | 5U,9C | 7U,9C | 1C | 0 | 0 | 0 | 0 | 0 |
| Soybean | 5C,9G | 5C,9G | 3H | 0 | 0 | 0 | 0 | 0 |
| Rice | 3C,9G | 5C,9G | 2G | 0 | 0 | 0 | 0 | 0 |
| Sorghum | 5U,9C | 10C | 2C,5G | 0 | 0 | 0 | 0 | 0 |

|  | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 |
|---|---|---|---|---|---|---|---|---|---|---|
| Rate kg/ha | 0.4 | 0.4 | 0.4 | 0.4 | 0.4 | 0.4 | 0.4 | 0.4 | 0.4 | 0.4 |
| | | | | | PRE-EMERGENCE | | | | | |
| Morningglory | 9G | 9G | 9C | 9G | 8H | 9G | 10C | 9C | 9C | 1C,8G |
| Cocklebur | 9H | 9H | 9H | 9H | 9H | 9H | 9H | 9H | 9H | 1H |
| Cassia | 6C,9G | 3C,5H | 8G | 3C,8G | 3H | 8G | 2C,9G | 5C,8G | 2C,9G | 3C |
| Nutsedge | 10E | 7G | 10E | 1C,9G | 0 | 10E | 10E | 10E | 9G | 1C |
| Crabgrass | 2C | 2C | 1H | 2C,5G | 2G | 2C,6G | 5C,9G | 2C,8G | 5C,9G | 1C,5G |
| Barnyardgrass | 3C | 2C,6H | 3C,9G | 3C,9H | 0 | 2C,9H | 9H | 4C,9G | 9C,9H | 2C,6H |
| Wild Oats | 0 | 2C,5G | 2C,6G | 1C,5G | 0 | 5G | 1C,8G | 2C,8G | 4C,9G | 5G |
| Wheat | 0 | 9G | 7G | 2C,9H | 0 | 5G | 9G | 7G | 2C,9G | 6G |
| Corn | 2C,9H | 9G | 2C,9H | 10H | 1C,3G | 9G | 5C,9G | 9G | 10H | 2C,8G |
| Soybean | 9G,2H,7X | 2C,6H | 2C,7H | 9H | 1C | 9H | 9H | 8H | 9H | 1C |
| Rice | 3C,8G | 10E | 3C,9H | 10E | 2C,6G | 2C,8G | 10E | 5C,9H | 10E | 4C,8H |
| Sorghum | 7H | 5C,9H | 9H | 8C,9H | 1C,3G | 9G | 6C,9G | 2C,9G | 5C,9H | 3C,9G |

|  | Cmpd. 11 | Cmpd. 12 | Cmpd. 13 | Cmpd. 14 | Cmpd. 15 | Cmpd. 16 | Cmpd. 17 | Cmpd. 18 | Cmpd. 19 | Cmpd. 20 | Cmpd. 21 |
|---|---|---|---|---|---|---|---|---|---|---|---|
| Rate kg/ha | 0.4 | 0.4 | 0.4 | 0.4 | 0.4 | 0.4 | 0.4 | 0.4 | 0.4 | 0.4 | 0.4 |
| | | | | | | PRE-EMERGENCE | | | | | | |
| Morningglory | 8G | 9G | 9G | 8G | 9G | 0 | 1C,5H | 9G | 5C,9G | 9C | 9G |
| Cocklebur | 4C,9G | 2C,5H | 9G | 8H | 8H | 0 | 3G | 9H | 9H | 9H | 9H |
| Cassia | 3C | 2C | 2C | 5G | 2C | 0 | 2C | 9G | 4C,7G | 2C,8G | 4C,9G |
| Nutsedge | 3G | 2C,8G | 3G | 4G | 5G | 0 | 0 | 10E | 10E | 10E | 10E |
| Crabgrass | 2C | 2C | 1C | 0 | 1C,3G | 0 | 0 | 2C,9G | 9G,4C | 4C,9G | 5C,9G |
| Barnyardgrass | 3C,9H | 2C | 1C,3G | 4G | 8H,2C | 0 | 1C | 9H | 9H | 9H | 9H |
| Wild Oats | 4G | 0 | 2G | 2G | 5G | 0 | 0 | 1C,8G | 4C,9H | 3C,9H | 4C,9H |
| Wheat | 6G | 0 | 7G | 2G | 8G | 0 | 0 | 9G | 9H | 9H | 3C,9H |
| Corn | 2C,8G | 2C | 2C,8G | 1C,6G | 9G | 0 | 0 | 9G | 9H | 9H | 10E |
| Soybean | 2C,6G | 1H | 1C | 1C | 2C | 0 | 0 | 9H | 9H | 9H | 9H |
| Rice | 3C,8G | 4G | 5C,8H | 1C,6G | 5C,9H | 0 | 0 | 10E | 10E | 10E | 10E |
| Sorghum | 2C,9G | 5G | 3C,8H | 2C,7H | 3C,9H | 0 | 0 | 5C,9H | 5C,9G | 6C,9G | 6C,9H |

|  | Cmpd. 22 | Cmpd. 23 | Cmpd. 24 | Cmpd. 25 | Cmpd. 26 | Cmpd. 27 | Cmpd. 28 | Cmpd. 29 | Cmpd. 30 | Cmpd. 31 | Cmpd. 32 |
|---|---|---|---|---|---|---|---|---|---|---|---|
| Rate kg/ha | 0.4 | 0.4 | 0.4 | 0.4 | 0.4 | 0.4 | 0.4 | 0.4 | 0.4 | 0.4 | 0.4 |
| | | | | | | PRE-EMERGENCE | | | | | | |
| Morningglory | 3C,6G | 2C | 6G | 9G | 2C,9G | 9G | 1C,3H | 2C | 9C | 2C,4H | 0 |
| Cocklebur | 9H | 3H | 2H | 5H | 2C | 7H | 0 | 2G | 9H | 2C,6H | 0 |
| Cassia | 3C | 2C | 1C | 2C | 2C | 2C | 2C | 2C | 5C,9G | 3C | 0 |
| Nutsedge | 10E | 1C | 0 | 1C | 0 | 0 | 1C,8G | 4G | 10E | 2C,5G | 0 |
| Crabgrass | 4G | 3G | 0 | 3G | 2G | 1C,5G | 2G | 2G | 2C,9G | 3C,6G | 0 |
| Barnyardgrass | 3C,8G | 4C,8G | 2C | 2C,5G | 4G | 2C,8H | 1C | 1C,2H | 2C,9G | 9H | 0 |
| Wild Oats | 2C,8G | 8G | 0 | 2C | 1C | 2C | 0 | 3G | 2C,9G | 2C,4G | 0 |
| Wheat | 2C,8G | 1C,8G | 0 | 1C,7G | 2G | 1C,9G | 0 | 2G | 2C,9G | 5C,9H | 0 |
| Corn | 3C,8H | 4C,8H | 2C,4G | 2C,8G | 2C,7G | 2C,9G | 1C | 1C,3G | 3C,9G | 10H | 1C,3H |
| Soybean | 1C,2H | 3G | 0 | 0 | 0 | 1C,2G | 1C,1H | 2G | 9H | 2C,6H | 0 |
| Rice | 9H | 2C,8H | 1C | 2G | 0 | 3G | 0 | 1C | 10E | 9H | 1C |
| Sorghum | 2C,9G | 2C,9G | 1C,5G | 1C,9G | 2C,4G | 5C,9H | 1C | 1C,7G | 2C,9H | 6C,9H | 2C,4H |

|  | Cmpd. 33 | Cmpd. 34 | Cmpd. 35 | Cmpd. 36 |
|---|---|---|---|---|
| Rate kg/ha | 0.4 | 0.4 | 0.4 | 0.4 |
| | PRE-EMERGENCE | | | |
| Morningglory | 0 | 0 | 0 | 0 |
| Cocklebur | 0 | 0 | 0 | 0 |
| Cassia | 0 | 0 | 0 | 0 |
| Nutsedge | 0 | 0 | 0 | 0 |
| Crabgrass | 0 | 0 | 0 | 0 |
| Barnyardgrass | 0 | 0 | 0 | 0 |
| Wild Oats | 0 | 0 | 0 | 0 |
| Wheat | 0 | 0 | 0 | 0 |
| Corn | 0 | 0 | 0 | 0 |
| Soybean | 0 | 0 | 0 | 0 |
| Rice | 0 | 0 | 0 | 0 |
| Sorghum | 0 | 0 | 0 | 0 |

It is noted that certain compounds tested showed no activity at the levels tested but it is thought they would have activity at higher levels.

TEST B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Da-*

*tura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

It should be noted that some of the compounds tested are useful as pre- or post-emergence treatment for weed control in crops such as wheat.

TABLE 8

PRE-EMERGENCE ON FALLSINGTON SILT LOAM

| | Compound 1 | | Compound 2 | | Compound 3 | | Compound 4 | | Compound 6 | | Compound 7 | | Compound 8 |
|---|---|---|---|---|---|---|---|---|---|---|---|---|---|
| Rate kg/ha | .060 | .250 | .060 | .250 | .060 | .250 | .060 | .250 | .060 | .250 | .060 | .250 | .060 |
| Crabgrass | 0 | 0 | 0 | 0 | 0 | 3G | 0 | 0 | 0 | 0 | 0 | 6G | 0 |
| Barnyardgrass | 0 | 0 | 0 | 0 | 0 | 3G | 2G | 4G | 0 | 4G | 4G | 8G,5H | 0 |
| Sorghum | 2G | 4G | 6G,3H | 8G,5H | 0 | 4G,2H | 7G,5H | 9G,9C | 3G | 6G,3H | 9G,9C | 10C | 4G,3H |
| Wild Oats | 0 | 0 | 0 | 0 | 0 | 0 | 0 | 3G | 0 | 0 | 3G | 2G | 0 |
| Johnsongrass | 0 | 5E | 5G,3H | 5G,5H | 0 | 4G | 7G,5H | 8G,5H | 0 | 3H | 7G,5H | 8G,5H | 0 |
| Dallisgrass | 0 | 0 | 0 | 0 | 0 | 0 | 0 | 0 | 0 | 0 | 2G | 3G | 0 |
| Giant foxtail | 0 | 0 | 0 | 0 | 0 | 3G | 0 | 5G,3H | 0 | 0 | 5G,2C | 8G,5H | 0 |
| Ky. bluegrass | 0 | 3G | 0 | 3G | 0 | 4G | 0 | 0 | 0 | 3G | 5G | 6G | 0 |
| Cheatgrass | 0 | 0 | 0 | 3G | 0 | 0 | 0 | 5G | 0 | 0 | 5G | 5G,2C | 0 |
| Sugarbeets | 3G | 7G,5H | 0 | 5G,3H | 3G | 8G,8C | 6G | 8G,8C | 4G | 6G | 7G,5H | 8G,8C | 6G |
| Corn | 0 | 0 | 0 | 0 | 0 | 0 | 0 | 5G,3H | 0 | 0 | 3G | 2C | 0 |
| Mustard | 8G,5C | 9G,8C | 4G | 5G,5H | 7G,5H | 9G,8C | 5G,3H | 7G,5H | 9G,9C | 10C | 7G,3H | 8G,8C | 8G,8C |
| Cocklebur | 0 | 0 | 0 | 0 | 0 | 0 | 0 | 0 | 0 | 0 | 0 | 0 | 0 |
| Pigweed | 6G | 9G,9C | 3G | 10C | 3G | 9G,9C | 0 | 9G,8C | 10E | 10E | 0 | 5G | 5G,5C |
| Nutsedge | 0 | 0 | 0 | 0 | 0 | 0 | 0 | 0 | 0 | 9G | 0 | 5G | 5G |
| Cotton | 0 | 0 | 0 | 2G | 0 | 0 | 0 | 4G,3H | 0 | 4G | 0 | 5G,5H | 2H |
| Morningglory | 0 | 0 | 0 | 3G | 0 | 3H | 0 | 5G,5H | 0 | 3G | 4G,5H | 8G,5C | 0 |
| Cassia | 0 | 0 | 0 | 0 | 0 | 3G | 0 | 3G | 0 | 3G | 0 | 8G,3C | 0 |
| Teaweed | 0 | 0 | 0 | 0 | 0 | 6G,3C | 0 | 0 | 0 | 5G | 3G | 5G,2C | 5G,2C |
| Velvetleaf | 0 | 3G,3H | 0 | 0 | 0 | 3G,3H | 0 | 2C | 5G,3H | 7G,5H | 2G | 5G,3H | 3G,3H |
| Jimsonweed | 0 | 0 | 0 | 0 | 0 | 0 | 0 | 2G | 0 | 5G,5C | 0 | 5G,3C | 5G,3C |
| Soybean | 0 | 0 | 0 | 2G | 0 | 2G | 0 | 4G,2H | 3G | 5G,2H | 3G | 7G,3C | 0 |
| Rice | 0 | 0 | 4G | 6G,3H | 3G | 5G | 3G | 7G,3H | 3G | 5G | 5G | 7G,3C | 4G |
| Wheat | 0 | 0 | 0 | 0 | 0 | 0 | 0 | 3G | 0 | 3G | 3G | 3G | 0 |

| | | Compound 8 | Compound 9 | | Compound 18 | | Compound 19 | | Compound 20 | | Compound 21 | |
|---|---|---|---|---|---|---|---|---|---|---|---|---|
| | Rate kg/ha | .250 | .060 | .250 | .030 | .120 | .030 | .120 | .030 | .120 | .030 | .120 |
| | Crabgrass | 0 | 3G | 6G | 5G | 6G | 4G | 6G,3C | 4G | 5G | 5G | 7G,3C |
| | Barnyardgrass | 6G,2H | 7G,3H | 8G,7C | 3G | 4G | 2G | 4G | 3G | 3G | 2G | 5G |
| | Sorghum | 8G,5H | 10C | 10C | 7G,3H | 9G,3H | 9G,5H | 10C | 4G,3H | 6G,5H | 9G,9C | 10C |
| | Wild Oats | 3G | 2G | 4G | 0 | 0 | 3G | 6G | 0 | 3G | 4G | 6G |
| | Johnsongrass | 3H | 7G,5H | 8G,5H | 4G | 6G,3H | 7G,3H | 8G,5H | 2G | 5G,3H | 5G | 7G,3H |
| | Dallisgrass | 3G | 3G | 6G | 0 | 0 | 0 | 2G | 0 | 0 | 2G | 3G |
| | Giant foxtail | 3G | 8G,5H | 9G,9C | 0 | 4G | 3G | 7G,5H | 0 | 4G,3C | 6G,3C | 8G,5H |
| | Ky. bluegrass | 3G | 6G | 7G,3C | 3G | 5G | 6G,3H | 6G,5C | 3G | 5G | 7G,7C | 8G,8C |
| | Cheatgrass | 3G | 8G,8C | 8G,9C | 0 | 5G | 8G | 10E | 0 | 5G | 8G | 10E |
| | Sugarbeets | 7G,5C | 8G,8C | 9G,9C | 4G,3H | 6G,3H | 4G,3H | 6G,5H | 3G | 7G,5H | 6G,5H | 7G,7C |
| | Corn | 4G,3H | 6G,5H | 8G,5H | 0 | 3G,3H | 0 | 6G,5H | 0 | 3G | 3G | 9G,9C |
| | Mustard | 9G,9C | 10C | 10C | 7G,7C | 9G,9C | 4G | 7G,8C | 8G,3C | 8G,8C | 6G,3H | 8G,8C |
| | Cocklebur | 3H | 5G,4H | 6G,5H | 0 | 4G,3H | 0 | 0 | — | 3G | 3G | 3G |
| | Pigweed | 10E | 8G | 10E | 0 | — | — | — | — | — | — | — |
| | Nutsedge | 8G | 4G | 7G | 7G | 9G,5C | 0 | 0 | 0 | 6G | 0 | 5G |
| | Cotton | 6G,5H | 4G | 8G,5H | 3G | 4G,3H | 0 | 3G | 0 | 0 | 0 | 3G |
| | Morningglory | 3G,5H | 7G,5H | 9G,5C | 0 | 0 | 0 | 4G,3H | 0 | 0 | 4G,3H | 7G,5H |
| | Cassia | 4G | 8G,3C | 9G,5C | 3G | 4G | 0 | 0 | 0 | 0 | 0 | 2C |
| | Teaweed | 6G,2C | 5G,2C | 6G,2C | 6G | 6G | 4G | 3G | 0 | 3G | — | 3G |
| | Velvetleaf | 8G,5H | 3G,3H | 6G,5H | 4G | 5G,3H | 0 | 3G | 0 | 3G | 0 | 2G |
| | Jimsonweed | 5G,3C | 7G,5C | 8G,8C | 0 | 5G,5C | 0 | 3G | 0 | 5G,3C | 4G | 7G,3C |
| | Soybean | 4G,2C | 3G,2C | 8G,5H | 3G | 5G | 3G | 2G,2C | 0 | 2G | 0 | 3G |
| | Rice | 5G | 9G,9C | 10E | 0 | 5G,3H | 7G,3H | 10E | 3G | 4G | 7G,3H | 9G,9C |
| | Wheat | 4G | 4G | 5G | 0 | 2G | 3G | 5G | 0 | 0 | 4G | 6G |

TEST C

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (*Digitaria sp.*), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a non-phytotoxic solvent. Two weeks after treatment, all species were compared to untreated controls and visually rated for response to treatment. The rating system was as described previously for Test A. The data are presented in Table C. Selected compounds tested by this procedure are useful for the post-emergence control of weeds in wheat, corn, rice and soybeans.

TABLE C
Over-the-Top Soil/Foliage Treatment

| | Compound 1 | | Compound 2 | | Compound 3 | | Compound 4 | | Compound 6 | | Compound 7 | | Compound 8 | |
|---|---|---|---|---|---|---|---|---|---|---|---|---|---|---|
| | 0.500 | 0.125 | 0.125 | 0.031 | 0.125 | 0.031 | 0.125 | 0.031 | 0.125 | 0.031 | 0.125 | 0.031 | 0.125 | 0.031 |
| Soybeans | 9G,9C | 10G,3C | 8G,5C | 4G,3C | 8G,4C | 9G,1C | 8G,7C | 8G,6C | 9G,9C | 10G,2C | 10G,4C | 10C | 10G,3C | 10G,6C |
| Velvetleaf | 10G,6C | 10C | 2C | 1C | 8G,3C | 7G,5C | 9G,7C | 9G,5C | 10C | 9G,5C | 9G,8C | 10C | 9G,5C | 10C |
| Sesbania | 9G,6C | 9G,7C | 0 | 0 | 7G,5C | 8G,4C | 9G,5C | 3C | 10C | 10C | 10C | 10C | 10C | 10C |
| Cassia | 6G,3C | 10G,1C | 4G | 0 | 7G | 7G | 3G,2C | 3C | 10G,5C | 10G,5C | 10G,5C | 9G,4C | 9G,4C | 7G,4C |
| Cotton | 6G | 6C | 1C | 0 | 3G | 6G,2C | 3C | 1G | 9G,5C | 9G,4C | 9G,9C | 9G,8C | 6G | 8G,4C |
| Morningglory | 9G,3C | 8G,8C | 6G,5C | 6G,3C | 8G,5C | 7G,5C | 6G,2C | 1G,1C | 9G,8C | 10C | 9G,8C | 9G,8C | 9G,9C | 10G,2C |
| Alfalfa | 6G,2C | 9G,9C | 1C | 1C | 1C | 5G | 6G,3C | 8G,6C | 10C | 10C | 10G | 10C | 0 | 7G |
| Jimsonweed | 5G | 4G,6C | 0 | 0 | 1C | 0 | 7G | 4G,5C | 7G,6C | 7G | 8G | 8G | 9G | 5G |
| Cocklebur | 2G | 8G,1C | 0 | 0 | 8G,2C | 3G,3C | 8G | 8G,8C | 10G,9C | 2G,2C | 8G,4C | 1G | 8G | — |
| Sunflower | 10G,2C | 9G,5C | 0 | 0 | 9G,7C | 2C,1H | 9G,7C | 9G,9C | 10G,5C | 0G,1C | 10G,5C | 8G | 9G,4C | 9G,2C |
| Mustard | 10C | 10C | 9G,9C | 9G,6C | 10C | 8G,7C | 9G,5C | 7G | 10C | 7G | 10C | 10C | 6G | 8G |
| Sugarbeets | 7G | 9G,5C | 8G,5C | 5G | 8G | 9G | 8G | 8G,3C | 10C | 10C | 9G,8C | 9G,5C | 3G | 8G |
| Corn | 3G | 2U | 3G | 5G,2C | 5G,2H | 8G,4C | 9G,7U | 9G,9C | 8G,8C | 8G,7C | 9G,2U | 9G,2C | 3G,3H | 9G,2C |
| Crabgrass | 0 | 0 | 1C | 5G,1C | 8G,5H | 3G | 9G,3U | 7G,3G | 5G | 6G | 10C | 10C | 0 | 3G |
| Rice | 0 | 0 | 2C | 0 | 3G | 2C | 1C | 1G,2C | 6G | 4G | 9G | 9G,2U | 1G | 6G |
| Nutsedge | 6G | 7G | 0 | 4G | 0 | 6G | 6G,3C | 5G,1C | 4G | 6G | 5G | 8G,2C | 6G | 6G |
| Barnyardgrass | 0 | 8G | 0 | 3G | 5G | 2G | 6G,3H | 8G,3C | 8G | 3G | 3G | 3G | 6G,2C | 4G,4H |
| Wheat | 0 | 0 | 0 | 0 | 2G | 6G | 4G | 3G | 3G,2C | 0 | 8G,6C | 8G,4C | 4G,4H | 7G,5C |
| Giant foxtail | 0 | 0 | 0 | 0 | 4G | 2G | 3G | 0 | 0G,1C | 0 | 5G,5C | 5G | 4G | 3G |
| Wild Oats | 2G | 0 | 0 | 0 | 6G,2C | 2C | 4G | 5G,3C | 8G | 0 | 9G | 8G | 2G | 3G |
| Sorghum | 0 | 0 | 7G | 6G | 8G,2H | 2C | 7G,2U | 0 | 3G | 5G | 7G,5C | 9G,5C | 7G | 2G |
| Johnsongrass | 0 | — | — | — | — | — | 4G | 7G,6U | 5G | 3G | 10G,5U | — | 2H | 5G |
| Field Bindweed | 3G | — | — | — | — | — | 8G | 0 | — | — | — | — | — | — |

| | Compound 8 | Compound 9 | | Compound 10 | | Compound 11 | | Compound 18 | | Compound 19 | | Compound 20 | | Compound 21 | | Compound 22 | | Compound 23 | |
|---|---|---|---|---|---|---|---|---|---|---|---|---|---|---|---|---|---|---|---|
| Rate kg/ha | 0.500 | 0.500 | 0.125 | 0.125 | 0.031 | 0.500 | 0.125 | 0.125 | 0.031 | 0.125 | 0.031 | 0.125 | 0.031 | 0.125 | 0.031 | 0.125 | 0.031 | 0.125 | 0.031 |
| Soybeans | 8G,5C | 10G,5C | 9G,8C | 9G,6C | 2G,1C | 8G,5C | 5G,5C | 10C | 10C | 9G,7C | 7G,6C | 9G,8C | 9G,7C | 10G,3C | 9G,8C | 7G,4C | 6G,3C | 5G | 3G |
| Velvetleaf | 8G,9C | 8G,7C | 7G,5C | 7G,5C | 4G,4C | 4G,3C | 0 | 10C | 10C | 6G | 6G,2C | 9G,4C | 6G | 9G,5C | 5G,4C | 7G,4C | 5G,2C | 0 | 0 |
| Sesbania | 10C | 9G,9C | 9G,8C | 8G,4C | 5G | 2C | 5G,4C | 10C | 10C | 9G,9C | 3G,3C | 9G,9C | 7G,7C | 8G | 4G | 7G,6C | 4G | 2G,2C | 2G |
| Cassia | 10G | 9G,5C | 9G,5C | 9G,7C | 0 | 5G,3C | 2G,3C | 2C | 9G,9C | 9G,9C | 0 | 1G,1C | 9G,8C | 5G,6C | 9G,4C | 8G | 8G,6C | 2G | 2G |
| Cotton | 9G,4C | 10G,9C | 10G,10C | 9G,9C | 9G,7C | 5G,3C | 4G | 1C | 10C | 9G | 9G | 3G | 7G,7C | 9G,3C | 9G,5C | 8G | 7G,3C | 0 | 2C |
| Morningglory | 10G,2C | 9G,9C | 10G,7C | 9G,5C | 8G,3C | 7G | 1G | 10C | 9G,9C | 6G,6C | 2G,3C | 9G,7C | 8G,2C | 9G,3C | 8G,3C | 8G,2C | 7G,3C | 2C | 2G |
| Alfalfa | 7G,3C | 7G,4C | 6G,4C | 2G,4C | 3G | 5G | 0 | 10C | 10C | 9G,3C | 8G | 9G,7C | 6G,3C | 10C | 9G,2C | 4G,3C | 2G | 2C | 2C |
| Jimsonweed | — | 6C | 4C | — | — | 0 | 0 | 9G,7C | 9G,4C | 9G | 0 | — | 6G,2C | 9G,7C | 8G,3C | 4G | 0 | 0 | 0 |
| Cocklebur | 10G | 10C | 10G,7C | 10G,3C | 2G | 10G,4C | — | 9G,9C | 9G,7C | 8G | 2C | 8G | 6G | 9G,7C | 9G,2C | 4G | 2G | 2C | 0 |
| Sunflower | 9G,7C | 10C | 10C | 8G,3C | 5G,2C | 6G,6C | 0 | 10C | 10C | 8G | 0 | 10C | 6G | 9G,5C | 6G | 2G,3C | 1G | 2C | 0 |
| Mustard | 10C | 10C | 10C | 9G,9C | 8G,5C | 9G,5C | 3G | 10C | 10C | 10C | 7G | 10C | 9G,9C | 8G,7C | 10C | 10C | 7G,5C | 4G,4C | 2C |
| Sugarbeets | 9G,2C | 9G,7C | 8G,6C | 8G,4C | 8G,5C | 9G | 4G | 10C | 9G,3C | 9G | 2G,3C | 9G | 8G | 5G | 5G | 2G | 4G | 4G | 2C |
| Corn | 9G,1C | 10C | 10C | 7G,1H | 7G,1C | 3G | 9G | 9G,9C | 8G | 9G,7C | 8G | 7G,7C | 7G,3H | 9G,7C | 10C | 10C | 0 | 4G | 2C |
| Crabgrass | 5G | 8G,3C | 8G,3C | 1G | 7G,1C | 3G | 4G | 8G | 7G | 3G | 5G | 7G | 0 | 8G,6C | 4G,3C | 2G | 0 | 0 | 3G |
| Rice | 5G | 9G,6C | 9G,4C | 5G | 8G,1C | 2G | 4G,2C | 5G,2C | 7G | 0 | 5G | 7G | 0 | 8G,4C | 10C | 3G,2H | 0 | 0 | 2G |
| Nutsedge | 8G | 3G | 3G | 4G | 9G,2C | 7G | 0 | 10C | 10C | 0 | 8G,7C | 6G,4C | 0 | 10C | 10C | 3G | 0 | 2C | 0 |
| Barnyardgrass | 7G,5C | 8G,7C | 7G,5C | 7G,4C | 8G,5C | 7G | 8G,4C | 9G,4C | 9G,3C | 0 | 0 | 9C | 8G | 10C | 2G | 8G,4C | 5G,5C | 8G,4C | 4G |
| Wheat | 6G | 7G,3C | 7G | 5G | 6G,2C | 5G | 0 | 9G,5C | 9G,3C | 8G | 6G | 8G | 6G | 5G | 9G,8C | 1G | 0 | 1G | 0 |
| Giant foxtail | 3G | 9G,5C | 8G,3C | 7G | 6G,2C | 5G | 5G | 9G,5C | 8G | 9G,8C | 8G,2C | 8G,2C | 5G | 9G,8C | 9G,2C | 8G,4C | 7G,5C | 2G | 2G |
| Wild Oats | 3G | 6G | 5G | 2G | 3G | 5G | — | 9C,7C | 7G | 9G,7C | 7G | 8G,4C | 5G,1C | 7G | 9G,2C | 1G | 4G | 3G | 0 |
| Sorghum | 7G,1C | 9G,7U | 9G,4U | 8G,1C | 9G,1U | 8G,1U | 6G,2U | 9G,8U | 5G | 6G,4C | 4G,5C | 8G,6C | 8G | 10C | 8G,5C | 6G | 0 | 6G | 4G |
| Johnsongrass | — | — | — | — | — | — | — | — | — | — | — | 8G,7U | 7G,3G | — | — | 6G | 5G,5C | 6G | 0 |
| Field Bindweed | — | — | — | — | — | — | — | — | — | — | — | 5G | 8G | — | — | 3G | 0 | 3G | — |

TEST D

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), smartweed (*Polygonum pensylvanicum*), tumble mustard (*Sisymbrium altissium*) kochia (*Kochia scoparia*), shepherd's purse (*Capsella bursa-pastoris*), *Matricaria inodora*, black nightshade (*Solanum nigrum*), yellow rocket (*Barbarea vulgaris*), wild mustard (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1–15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table D. One of the compounds has utility for pre- and or post-emergence weed control in wheat and barley.

TABLE D

| | Compound 1 | | | | Compound 2 | |
|---|---|---|---|---|---|---|
| | 1/2 Pre-Emergence | | 1 Post Emergence | | Pre-Emergence | Post-Emergence |
| Rate kg/ha | ½ | 1 | ½ | 1 | ⅛ | ⅛ |
| wheat | 1C,1G | 1C,2G | 1C,1G | 0 | 7G | 4C, 7G |
| barley | 6G | 1G | 2C | 1C | 8G | 5C, 6G |
| wild oats | 1C,2G | 1C,3G | 1C | 0 | 2C,6G | 5C, 6G |
| downy brome | 5G | 5G | 0 | 0 | 10C | 7C, 9G |
| cheatgrass | 1C,6G | 2C,8G | 0 | 0 | 10C | 10C |
| blackgrass | 4G | 1C,5G | 2G | 0 | 6C,8G | 5C, 8G |
| annual bluegrass | 1C,5G | 4G | 0 | 5G | 7C,9G | 6C, 8G |
| green foxtail | 4G | 6G | 2G | 2C,5G | 8C,9G | 9C, 9G |
| quackgrass | 5G | 6G | 2G | 4G | 4C,8G | 5C, 9G |
| Italian ryegrass | 1C,4G | 1C,5G | 1G | 6G | 5C,8G | 4C, 7G |
| ripgut brome | 5G | 2C,7C | 3G | 3G | 6C,9G | 10C |
| Russian thistle | 0 | 0 | 1C,2G | 7C,8G | 5C,4G | 10C |
| tansy mustard | 10E | 10E | 10C | 10C | 10C | 10C |
| smartweed | — | — | — | — | — | — |
| tumble mustard | 10C | 10C | 10C | 10C | 10C | 10C |
| kochia | 3C,8G | 2C,8G | 3C,7G | 2C,8G | 9C,9G | 10C |
| shepherd's purse | 10C | 10C | 10C | 10C | 10C | 10C |
| *Matricaria inodora* | 9G | 9G | 10C | 10C | 9G | 10C |
| black nightshade | 6G | 8G | 0 | 3G | 3C,8G | 10C |
| yellow rocket | 9G | 9G | 10C | 10C | 8C,9G | 10C |
| wild mustard | 10C | 10C | 10C | 10C | 10C | 10C |
| wild buckwheat | 2C,8G | 2C,9G | 10C | 10C | 6C,7G | 10C |

TEST E

A series of simulated rice paddy tests were conducted in a greenhouse. Compounds selected from within the scope of the present invention were formulated and applied directly to the paddy water three days after transplanting of rice. "Early" plant response ratings (less than one week after application) were taken in some of the tests; "late" plant response ratings (5 to 6 weeks after application) were taken in all tests.

TABLE E

| Rate ai/ha | Rice Early | Rice Late | Barnyard-grass late | Water Chestnut late | Arrowhead late |
|---|---|---|---|---|---|
| | | | Compound 1 | | |
| 50 | — | 0 | 0 | 9G | 1G,2H |
| 200 | — | 0 | 0 | 3G | 0 |
| | | | Compound 6 | | |
| 50 | 0 | 0 | 10C | 10C | 4G |
| 200 | 0 | 0 | 9C | 10C | 5G,3H |
| | | | Compound 8 | | |
| 25 | 0 | 0 | 6G,8E | 5G | 9G |
| 100 | 0 | 0 | 9G,9E | 10C | 10G,5C |
| | | | Compound 18 | | |
| 50 | 0 | 4G | 8C | 10C | 6G |
| 200 | 0 | 0 | 9G | 10C | 10C |
| | | | Compound 22 | | |
| 50 | 0 | 0 | 0 | 0 | 0 |
| 200 | 0 | 0 | 0 | 0 | 0 |

Several of the compounds tested provided excellent control of weeds in rice without damage to the rice.

What is claimed is:

1. A compound selected from:

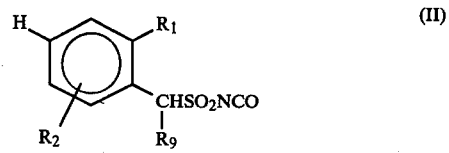

wherein
$R_1$ is F, Cl, Br, $CF_3$, $C_1$–$C_3$ alkoxy, $C_1$–$C_3$ alkyl, $NO_2$, $CO_2R_4$, $SO_2R_5$, $SO_2NR_6R_7$, $SO_2N(OCH_3)CH_3$, $SO_2OCH_2CF_3$, $OSO_2R_5$ or $CH_2L$;
L is $SO_2NR_6R_7$, $OCH_3$, $OC_2H_5$, $CO_2CH_3$ or $CO_2C_2H_5$;
$R_2$ is H, Cl, Br, F, $CF_3$ or $OCH_3$;
$R_4$ is $C_1$–$C_3$ alkyl, $CH_2CH=CH_2$, $CH_2CH_2Cl$, or $CH_2CH_2OCH_3$;
$R_5$ is $C_1$–$C_3$ alkyl or $CF_3$;
$R_6$ and $R_7$ are independently $C_1$–$C_3$ alkyl; and
$R_9$ is H or $C_1$–$C_3$ alkyl;
provided that the total number of carbon atoms of $R_6$ and $R_7$ is less than or equal to 4.

* * * * *